US011447742B2

(12) United States Patent
Hamill et al.

(10) Patent No.: US 11,447,742 B2
(45) Date of Patent: Sep. 20, 2022

(54) COMPOSITIONS AND METHODS FOR ACTIVATION AND OVEREXPRESSION OF SECONDARY METABOLITES IN MICROORGANISMS

(71) Applicant: Prospective Research, Inc., Beverly, MA (US)

(72) Inventors: Dakota Benjamin Hamill, Gloucester, MA (US); Jake J. Cotter, S. Hamilton, MA (US)

(73) Assignee: Prospective Research, Inc., Beverly, MA (US)

( * ) Notice: Subject to any disclaimer, the term of this patent is extended or adjusted under 35 U.S.C. 154(b) by 397 days.

(21) Appl. No.: 16/059,258

(22) Filed: Aug. 9, 2018

(65) Prior Publication Data

US 2018/0346871 A1  Dec. 6, 2018

Related U.S. Application Data

(63) Continuation of application No. PCT/US2017/017095, filed on Feb. 9, 2017.

(60) Provisional application No. 62/292,953, filed on Feb. 9, 2016.

(51) Int. Cl.
| | |
|---|---|
| C12P 1/04 | (2006.01) |
| C12N 1/38 | (2006.01) |
| C12N 15/80 | (2006.01) |
| C12N 1/12 | (2006.01) |
| C12P 17/04 | (2006.01) |
| C07D 307/33 | (2006.01) |
| C12P 17/16 | (2006.01) |
| C12P 1/06 | (2006.01) |

(52) U.S. Cl.
CPC ............. *C12N 1/38* (2013.01); *C07D 307/33* (2013.01); *C12N 1/12* (2013.01); *C12N 15/80* (2013.01); *C12P 1/04* (2013.01); *C12P 1/06* (2013.01); *C12P 17/04* (2013.01); *C12P 17/165* (2013.01)

(58) Field of Classification Search
CPC .. C12N 1/38; C12N 15/80; C12N 1/12; C12P 1/04; C12P 17/165; C12P 1/06; C12P 17/04; C07D 307/33
See application file for complete search history.

(56) References Cited

PUBLICATIONS

Hsiao et al. Analysis of Two Additional Signaling Molecules in Streptomyces coelicolor and the Development of a Butyrolactone-Specific Reporter System. Chemistry & Biology. 2009;16:951-960.*

Baltz, RH "Renaissance in antibacterial discovery from actinomycetes." Current Opinion in Pharmacology. 2008. 8 (5):557-563.
Biarnes-Carrera, M et al. "Butyrolactone signalling circuits for synthetic biology" Current Opinion in Chemical Biology. 2015. 28:91-98.
Chen, K et al., "Unusual odd-electron fragments from even-electron protonated prodiginine precursors using positive-ion electrospray mass spectrometry," Journal of the American Society for Mass Spectrometry, 2008. 19: 12, 1856-1866.
Epstein, S "Isolating "uncultivable" microorganisms in pure culture in a simulated natural environment." Science. 2002. 296.5570: 1127-1129.
Hsiao, NH et al. "Analysis of two additional signaling molecules in Streptomyces coelicolor and the development of a butyrolactone-specific reporter system" Chemistry & Biology. 2009. 16: 951-960.
Lewis, K "Platforms for antibiotic discovery" Nature Reviews Drug Discovery. 2013. 12: 371-387.
Morin , JB et al. "Replication of biosynthetic reactions enables efficient synthesis of A-factor, a γ-butyrolactone autoinducer from Streptomyces griseus" Organic and Biomolecular Chemistry. 2012. 10:1517-20. PMID: 22246070.
Nodwell, JR "Are you talking to me? A possible role for γ-butyrolactones in interspecies signalling" Molecular Microbiology. 2014. 94(3): 483-485.
Silver LL "Are natural products still the best source for antibacterial discovery? The bacterial entry factor." Expert Opin. Drug Discovery. 2008. 3(5): 487-500 (2008).
Silver, LL "Challenges of Antibacterial Discovery". Clinical Microbiology Reviews. 2011;24(1 ):71-109. doi:10.1128/CMR.00030-10.
Silver, LL "Natural products as a source of drug leads to overcome drug resistance" Future Microbiol. 2015. 10(11): 1711-1718.
International Search Report and Written Opinion of the International Search Authority received in in PCT/US17/17095 dated Jun. 2, 2017 (12 pgs.).
Antoraz, S et al. "Toward a new focus in antibiotic and drug discovery from the Streptomyces arsenal". 2015. Frontiers in Microbiology vol. 6, article 461, pp. 1-8.

(Continued)

Primary Examiner — Lynn Y Fan
(74) Attorney, Agent, or Firm — Sonia K. Guterman; Preeti T. Arun; Armis Intellectual Property Law, LLC

(57) ABSTRACT

Methods and compositions herein provide non-naturally occurring γ-butyrolactones (GBLs) in racemic mixtures that increase efficiency and effectiveness of screening for production of antibiotics, and enhance yields and express silent pathways. Non-naturally occurring GBLs were synthesized and found to stimulate antibiotic production in several different streptomycete strains. Antibiotic production by *Streptomyces coelicolor* was induced by a racemic mixture of non-cognate stereoisomers of VB-D, seven of which are non-naturally occurring. Further, novel A-factor-type GBL analogs stimulated antibiotic production in *S. coelicolor*. Synthesis in response to the treatment with the non-cognates GBL was observed for known compounds including undecylprodigiosin, desferrioxamine and streptorubin B, as was synthesis of a compound of unknown structure. A group of 37 additional microbial strains was screened by principal component analysis to determine optimal concentrations of each of a panel of four non-cognate synthetic GBLs for addition to cultures with optimal stimulation of secondary metabolites, and large scale fermentations were analyzed and product enhancement by the GBLs was observed.

7 Claims, 26 Drawing Sheets

(56) References Cited

PUBLICATIONS

Tan, GY et al. "Exogenous 1,4-butyrolactone stimulates A-factor-like cascade and validamycin biosynthesis in Streptomyces hygroscopicus 5008". 2013. Biotechnol. Bioeng. vol 110, No. 11, pp. 2984-2993.
Oikawa, Y et al. "Working with Hazardous Chemicals" 2014. Organic Syntheses, Coll. vol. 7, p. 359 (1990); vol. 63, p. 198 (1985). (5 pgs.).

* cited by examiner

COMPOSITIONS AND METHODS FOR ACTIVATION AND OVEREXPRESSION OF SECONDARY METABOLITES IN MICROORGANISMS

RELATED APPLICATION

The present application claims the benefit of U.S. provisional application Ser. No. 62/292,952 filed Feb. 9, 2016, entitled "Compositions and methods of activation and overexpression of secondary metabolic gene clusters in microorganisms", inventors Dakota Benjamin Hamill and Jake J. Cotter, and which is hereby incorporated herein in its entirety.

TECHNICAL FIELD

Methods and compositions are provided herein to activate in microorganisms secondary metabolic pathways that are silent or under expressed in laboratory conditions, and to identify and overexpress bioactive compounds and to discover products of silent pathways.

BACKGROUND

The number of new classes of antibiotics discovered over the past 25 years has been decreasing due to inefficiencies in the process of antibiotic discovery. See, Silver, L.; Expert Opin. Drug Discovery, 3(5): 487-500; Silver, Future Microbiol., 10(11): 1711-1718 (2015). In fact, no major classes of antibiotics have been introduced between 1962 and 2000. The most recently introduced antibiotic classes: linezolid, daptomycin, and retapamulin, were introduced in 2000, 2003, and 2007, respectively. These chemical classes: pleuromutilins, oxazolidinones, and acid lipopeptides, were first reported or patented in 1952, 1978, and 1987, respectively. See, Silver, Clinical Microbiology Reviews, 24(1):71-109 (2011). Antibiotic resistance has increased steadily during the same time period that antibiotic discovery has slowed. Antibiotic resistance is commonly the result of horizontal gene transfer and develops from environmental pressures. See, Silver, Future Microbiol., 10(11): 1711-1718 (2015).

In the 1950s, about 1,000 soil microbes were generally required to be isolated to be screened to find a new antibiotic. More than 10,000,000 soil microbes were required by the 1980s to be isolated and screened for the industry to produce a new antibiotic. The research approach was to screen more samples, instead of building tools to screen more effectively. This has led to a cost ineffective business model that resulted in decline of antibiotic discoveries during recent decades. For example, the actinomycete family of a soil bacteria, was previously the most important sources for antibiotics, yet these microorganisms have been nearly abandoned in recent years in favor of high-throughput target based screening of chemical libraries because of the lack of success with prior methods of discovery. See, Baltz, Current Opinion in Pharmacology, 8(5):557-563 (2008).

A small percentage of secondary metabolic pathways are thought to be active under laboratory culture conditions. See, Epstein, Science 296.5570: 1127-1129 (2002). Silent gene clusters and under expressed secondary metabolic gene clusters produce undetectable levels of bioactive compounds under laboratory conditions of culture and screening. Traditional laboratory techniques for bioactive compound screening include using fermentation broths for detection. See, Silver, Future Microbiol., 10(11): 1711-1718 (2015). This approach has been largely abandoned in favor of hypersensitive screening methods such as genomic strategies for activating known operons and pathways, for example, reporter strains screening, synergy screening, and antisense screening. Ibid. Few microorganisms from environmental samples produce bioactive compounds on known solid media in Petri dishes or in broth or liquid cultures due to absence of environmental signals that typically take place in the native community of the microorganism. Previous attempts to assemble these gene clusters in vitro for exogenous expression have been largely unsuccessful. Methods of gaining access to these pathways are clearly desirable. Such methods would transform microbiology and the healthcare system by accelerating drug discovery.

Streptomyces bacteria are a large family of Gram-positive actinomycetes, cells of which have an ensemble of biosynthetic pathways that generate small molecules with potent biological activities against other organisms including about 70% of antibiotics currently clinically used and drugs to treat other diseases such as fungal infections and cancer. See, Nodwell, Molecular Microbiology, 94(3): 483-485 (2014). Secondary metabolites have evolved to repel or attract other organisms as a survival mechanism. See, Silver L., Expert Opin. Drug Discovery, 3(5): 487-500 (2008).

Gamma (γ)-butyrolactones (GBLs) are an important family of signaling molecules that regulate antibiotic production. See, Nodwell, Molecular Microbiology, 94(3): 483-485 (2014). For example, antibiotic daunorubicin in Streptomyces peucetius, streptomycin in Streptomyces gricseus, virginiamycin in Streptomyces virginae, actinorhodin in Streptomyces coelicolor, undecylprodigiosin in S. coelicolor, and lankamycin in Streptomyces violaceceoniger are regulated by GBL signaling, and structures of these antibiotics are provided in FIG. 4. Structures of 14 known naturally occurring GBLs are shown in FIG. 5.

Most GBLs are produced in minute quantities. The biosynthetic pathways that regulate antibiotic production using GBLs as a primary intercellular signal are diverse. See, Biarnes-Carrera et al., Current Opinion in Chemical Biology, 28: 91-98 (2015). At least fourteen naturally occurring GBLs have been characterized, and are classified into groups: A-factor with 1'-keto group, which is the most common GBL used in research; virginiae butanolide (VB) with a 1'-α-hydroxyl; and IM-2 with a 1'-3-hydroxyl. See, Hsiao et al., Chemistry & Biology, 16: 951-960 (2009); Biarnes-Carrera et al., Current Opinion in Chemical Biology, 28: 91-98 (2015). A-factor was first characterized as an endogenously produced hormone that controls a gene cluster involved in sporulation and secondary metabolism in Streptomyces griseus. See, Hsiao et al., Chemistry & Biology, 16: 951-960 (2009). GBLs generally have specific and sensitive receptors. See, Biarnes-Carrera et al., Current Opinion in Chemical Biology, 28: 91-98 (2015). The specificity was demonstrated by the observation that A-factor analogs with one extra carbon or with fewer than eight carbons had a 10-fold lower activity than naturally occurring A-factor. See, Hsiao et al., Chemistry & Biology, 16: 951-960 (2009).

The number of antibiotics approved by the Food and Drug Administration has decreased from 16 in 1983-1987 to 2 in 2008-2012, see FIG. 1. As antibiotic resistance has sharply increased during this period, the need for new antibiotics has become more urgent.

SUMMARY

An aspect of the invention herein provides a composition for upregulating biosynthesis and production of a bioactive microbial product by cells of a sample of microorganisms, the composition including:

at least one synthetic non-naturally occurring derivative of a γ-butyrolactone (GBL) core, in a dose effective to increase expression of the genes and biosynthetic production of the product in the cells.

In an embodiment of the composition, the bioactive product has at least one activity selected from the group consisting of: anti-bacterial, anti-fungal, anti-viral, anti-helminthic, anti-cancer, anti-malarial, anti-trypanosomal, complement inhibitory, anti-spasmodic, toxin neutralizing, immune stimulant, anti-inflammatory, immune suppressant, diuretic, and herbicidal.

In certain embodiments of the composition, the sample of the microorganisms is a mixture of a plurality of strains or species, and the composition is effective to upregulate expression of genes in at least one of the strains or species. In an embodiment of the composition, the synthetic non-naturally occurring derivative of the GBL has a chemical structure different from naturally occurring GBLs, and the composition structure does not have the same as: *Streptomyces griseus* A-factor; *S. viridochromogenes* Factor I; *S. lavendulae* IM-2; *S. coelicolor* SCB1, SCB2, and SCB3; anthracyclines from *S. bikiensis*; *S. cyaneofuscatus* greater length hydrocarbon chains in 2R3R and 2S3S; and *S. virginiae* butanolides VB-A, VB-B, VB-C, VB-D, and VB-E. The term "non-naturally occurring" as used herein means a GBL having a chemical structure which is not found in nature, or is a stereoisomer or an enantiomer of a naturally produced GBL which is not found in nature.

In certain embodiments of the composition, the GBL comprises a core which is substituted at the 3 position by a group having the structure methyl-$R_1$ and at the 2 position by a group having the structure selected from ketone-$R_2$, alcohol-$R_2$, and carbonyl-$R_2$, wherein the substituent at the 2 and 3 position of the GBL are attached to the GBL core by recto (R) or levo (L) bonds, wherein $R_1$ and $R_2$ are each independently selected from the group consisting of: a lower alkane, an alkyne, an alkoxyl, an alkoxy, a halogen, a sulfide, an amine, a carbonyl, and an alkene selected from the group consisting of: an ethyl, an ethoxy, an ethoxyl, a propyl, a propoxy, a propoxyl, a butyl, a pentyl, a hexyl, a t-butyl, an s-butyl, an i-butyl, an i-pentyl, an i-hexyl, and an i-heptyl.

In an embodiment of the composition, the GBL core is substituted at the 2 or 3 position with a lower alkane having a length of 1 carbon to about 8 carbons. In certain embodiments of the composition, the GBL core is substituted at the 2 or 3 position with an alkane having a length greater than 8 carbons. In an embodiment of the composition, the $R_1$ includes hydroxyl and is either recto-(R) or levo-(L), and $R_2$ comprises a hexyl which is R or L. In certain embodiments the composition is selected from at least one enantiomer or stereoisomer of the group consisting of 3-(1-hydroxyethyl)-4-(hydroxymethyl)dihydrofuran-2(3H)-one; 3-(1-hydroxyheptyl)-4-(hydroxymethyl)dihydrofuran-2(3H)-one; 3-acetyl-4-(hydroxymethyl)dihydrofuran-2(3H)-one; and, 3-heptanoyl-4-(hydroxymethyl)dihydrofuran-2(3H)-one.

An aspect of the invention herein provides a method of improving a yield of a microbially-produced bioactive secondary metabolite product, the method including contacting cells of at least one strain of microorganism with a suitable amount of at least one γ-butyrolactone (GBL) composition such that the GBL is non-cognate to the strain or is synthetic and non-naturally occurring, and culturing the cells of the strain with the GBL under conditions for production of the product; and, obtaining the product from the cells by separation of cells and medium or purification of the product from the cells and analyzing the amount of the product, and determining that the yield of the product per unit of volume of culture or the yield of the product per weight of cells is greater than that from control cells of the strain not so contacted with the GBL composition and otherwise identically cultured and analyzed, and therefore the yield of the product from the cells cultured with the derivative of the GBL is improved compared to that from the control cells.

In an embodiment of the method, the strain of microorganism is bacterial. In certain embodiments of the method, the strain of bacteria is an actinomycete. In an embodiment of the method, the strain of microorganism is fungal or algal. In certain embodiments of the method, the derivative of the GBL is synthetic and non-naturally occurring and is at least one of the compositions selected from formulas I-VII in FIG. 10. In an embodiment of the method, a genus of the actinomycete selected from the group of genera consisting of: *Actinopolyspora*, *Amycolatopsis*, *Micromonospora*, *Nocardia*, *Pseudonocardia*, *Saccharothrix*, *Saccharopolyspora*, *Salinospora*, *Streptomyces*, *Tetinomedara*, and *Verrucosispora*. In certain embodiments of the method, the yield of the product from the cells contacted with the GBL is at least about two-fold great, four-fold great, ten-fold greater, or at least about twenty-fold greater than from the control cells. In certain embodiments of the method, the genus is *Streptomyces* and the species is selected from at least one of the group consisting of: *avermitilis*, *S. aureofaciens*, *S. capreolus*, *S. cattleya*, *S. clavuligerus*, *S. coelicolor*, *S. fradiae*, *S. garyphallus*, *S. griseus*, *S. kanamyceticus*, *S. levoris*, *S. lincolnensis*, *S. niveus*, *S. noursei*, *S. platensis*, *S. plicatus*, *S. pristinaespiralis*, *S. orientalis*, *S. ribosidfus*, *S. rimosus*, *S. roseosporus*, *S. scabiei*, *S. venezuelae*, *S. vinaceus*, and *S. virginiae*; or the genus is at least one *Pseudonocardia* species selected from the group of: *P. acacia*; *P. ailaonensis*; *P. adelaidensis*; *P. alaniniphila*; *P. ammonioxydans*; *P. carboxydivorans*; *P. halophobia*; *P. kujensis*; *P. nitrificans*; *P. petroleophila*; *P. salamisensis*; *P. sulfoxidans*; *P. thermophila*; and *P. zigingensis*; or the genus is *Amycolatopsis* and the species is at least one selected from the group of: *A. alba*, *A. azurea*, *S. balhimycena*, *A. coloradensis*, *A. fastidiosa*, *A. keratiniphila*, *A. lurida*, *A. mediterranei*, *A. orientalis*, *A. sulphurea*, *A. tolypomycina*, and *A. vancoresmycina*.

An aspect of the invention herein provides a method of discovery of a cell-produced secondary metabolic compound in a microbial strain containing putative unexpressed or under expressed genes encoding enzymes for biosynthesis of a chemical entity having a medicinal or industrial biological activity, the method including:

contacting cell samples containing cells from at least one microbial strain with at least one synthetic non-naturally occurring or non-cognate γ-butyrolactone (GBL) in an amount suitable for inducing secondary metabolite expression, such that the microbial strains are selected from the group of: fresh isolates from nature, a naturally occurring mixture of unpurified microorganisms, and an established species strain wherein the GBL and the established species are non-cognate;

culturing the cell samples with the GBL under conditions for production of the secondary metabolite chemical compounds;

screening the cultures by at least one detection system for presence of the biological activity, or by at least one detection system for presence of the metabolite not so expressed in control samples not contacted with the GBL and otherwise identical and further screening the metabolite for the biological activity, and the presence of the biological activity identifies the producing sample containing at least one strain of microorganism producing the chemical having the activity; and, characterizing at least one chemical structure having the biological activity, and comparing the structure to a library database of known chemical entities to obtain chemicals not previously known, thereby screening to discover the chemical compounds with the biological activity. In an embodiment of the method, the at least one microbial strain contains at least two, at least five, or at least 10 strains. In certain embodiments of the method, the GBL is a plurality of GBLs having non-identical chemical structures, and the plurality is at least two or at least five GBLs. In an embodiment of the method, the non-identical chemical structure includes a GBL which is a racemate, enantiomer, stereoisomer, or a racemic mixture. In certain embodiments of the method, screening further includes contacting each of the samples to the detection system for the biological activity, the detection system including at least one component selected from the group of: an enzyme, an organism, a tissue culture, a cell culture; the method further including measuring an activity selected from: antibacterial; antifungal; herbicidal; anti-helminthic; insecticidal; anti-viral; an anti-cancer; immune suppressant; anti-inflammatory; and anti-spasmodic. In an embodiment of the method, culturing cell samples is in a liquid medium, and the method further includes prior to screening, separating the cells from the medium to obtain a resulting supernatant depleted of the cells and a resulting cell pellet. In certain embodiments of the method, culturing cell samples is in contact with soil, and the method further includes prior to screening, separating the cells from the soil and washing the soil and cells, to obtain resulting components of supernatant, cell pellet, and soil, and assaying each for amount of the biological activity.

An embodiment of the method further includes after identifying, isolating the chemical compound from the producing culture contacted with the GBL. An embodiment of the method further includes isolating, from the plurality of GBLs contacted to the sample, the at least one GBL that induces expression of the product.

In an embodiment of the method, characterizing the chemical structure further includes analyzing by at least one method selected from the group consisting of: mass spectrometry (MS); gas chromatography; thin layer chromatography; matrix-assisted laser desorption/ionization (MALDI); MALDI-time of flight (MALDI-TOF); moving bed chromatography; and high performance liquid chromatography (HPLC). In certain embodiments of the method, culturing is growing the strain or strains on solid medium, and screening further includes adding cells of a target indicator strain comprising at least one of a bacterium, a fungus, a eukaryotic cell, a white blood cell, and a eukaryotic tissue explant. An embodiment of the method further includes testing a sample of the supernatant in a test subject, which is an experimental animal model of a disease.

An embodiment of the method further includes testing a sample of the supernatant in vivo in cultured cells or tissues of an organism selected from the group consisting of: a mammal; a fungus; a helminth; a plant; and, an insect.

An embodiment of the method further includes obtaining coordinates of peaks observed by MS, MALDI, MALDI-TOF, or HPLC corresponding to presence of secondary metabolism products, and comparing the location of the peaks to that of known previously characterized products to identify chemical entities, and further to characterize products from databases as previously identified chemicals, or as potentially novel chemical entities. An embodiment of the method further includes isolating and screening the cell sample strains for production of the novel chemical entities in presence of the GBL.

An aspect of the invention herein provides a method of increasing or accelerating production of a microbial secondary metabolism compound by a producing microorganism, the method including:

contacting a culture of the producing microorganism strain with a GBL at an effective dose to upregulate expression and production of the compound, for example, by inducing or by depressing operons of genes encoding enzymes that synthesize the compound, or by inactivating inhibitors of expression, such that the GBL is non-cognate to the strain or is a non-naturally occurring GBL. In certain embodiments, the GBL is added at or before inoculation of production culture medium cells of the strain. In an alternative embodiment of the method, the GBL is added after inoculation or during growth of cells of the strain. In another alternative embodiments of the method, the GBL is added at stationary phase or after cessation of growth of the cells of the strain. In another alternative embodiment of the method, the GBL is added at a plurality of time points during culture of the micro-organism.

An embodiment of the method further includes comparing amount of the secondary metabolism compound with that of a control culture not contacted with the GBL and otherwise identical. In an embodiment of the method, the effective dose of the GBL is about 0.2 μM-0.8 μM, 0.8μ-20 M, 20 μM-100 μM, or is greater than 100 μM.

An embodiment of the invention provides a novel chemical produced by a culture of *S. coelicolor* treated with at least one enantiomer or stereoisomer of 3-(1-hydroxyheptyl)-4-(hydroxymethyl)dihydrofuran-2(3H)-one, and eluting from a mass spec time of flight analysis with a peak at 1.84.

DETAILED DESCRIPTION

Figure 1:
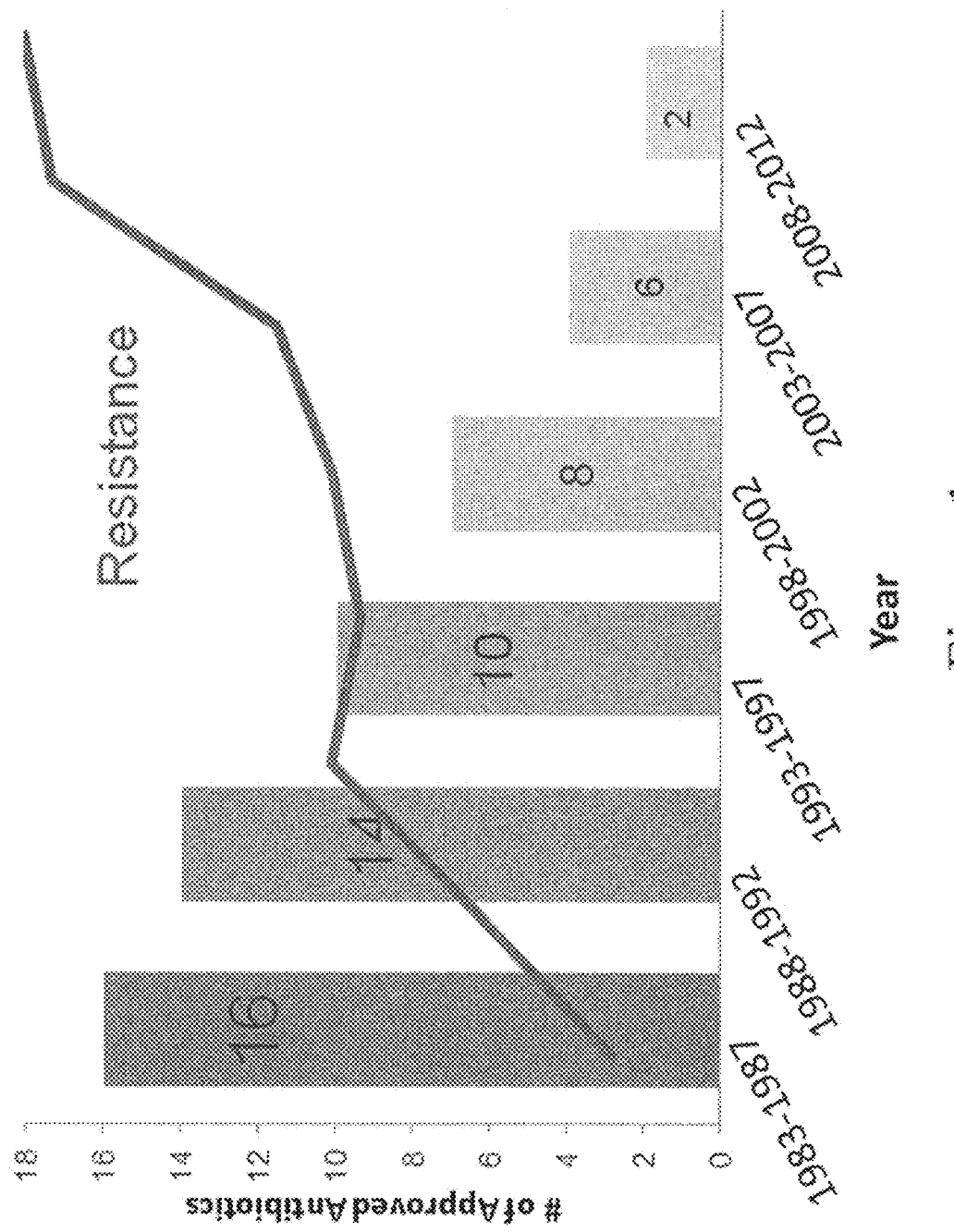
FIG. 1 is a bar graph of number of antibiotics approved in four year intervals from 1983-2012, and appearance of organisms with antibiotic resistance during this period. The line indicates increased incidence of resistance to antibiotics during this period.
Figure 2:
FIG. 2 is a photograph of each of an untreated control plate culture of *S. coelicolor* strain A3(2) and a plate culture of *S. coelicolor* that was treated by depositing a 2 μL volume 20 of a solution of a racemic mixture containing 165 μg of non-naturally occurring A-factor type GBLs indicated herein as X and XI (see, Example 6 and FIG. 8). The dark area on the treated plate indicates production of the purple antibiotic, actinorhodin.

Compositions and methods herein provide chemical tools that have the potential to accelerate and increase antibiotic discovery faster than ever before. These compositions and methods are part of a strategy to return to natural product discovery as a source of new antibiotics. The compositions and methods provided herein are potential chemical keys necessary to activate silent gene pathways. FIG. 2 shows activation in S. coelicolor of production of a purple antibiotic as a result of spotting on the bacteria a solution of a racemic mixture of non-naturally occurring GBLs having formulas VIII and IX. This results in discovery of new antibiotics faster and more cost effectively than using previous techniques, and increases the likelihood of finding novel structures.

An antibiotic biosynthesis operon is a group of genes that code for an antibiotic under similar or identical regulatory control. A challenge in finding new antibiotic leads is lack of keys to access the products of silent operons. There is an outstanding need for a technology platform to activate silent operons of microorganisms that potentially produce antibiotics. See, Lewis, *Nature Reviews Drug Discovery* 12: 371-387 (2013). Genomic data show that current approaches access only a small percentage of available secondary metabolic genes because most organisms fail to produce antibiotics upon culture in the laboratory.

Figure 4:
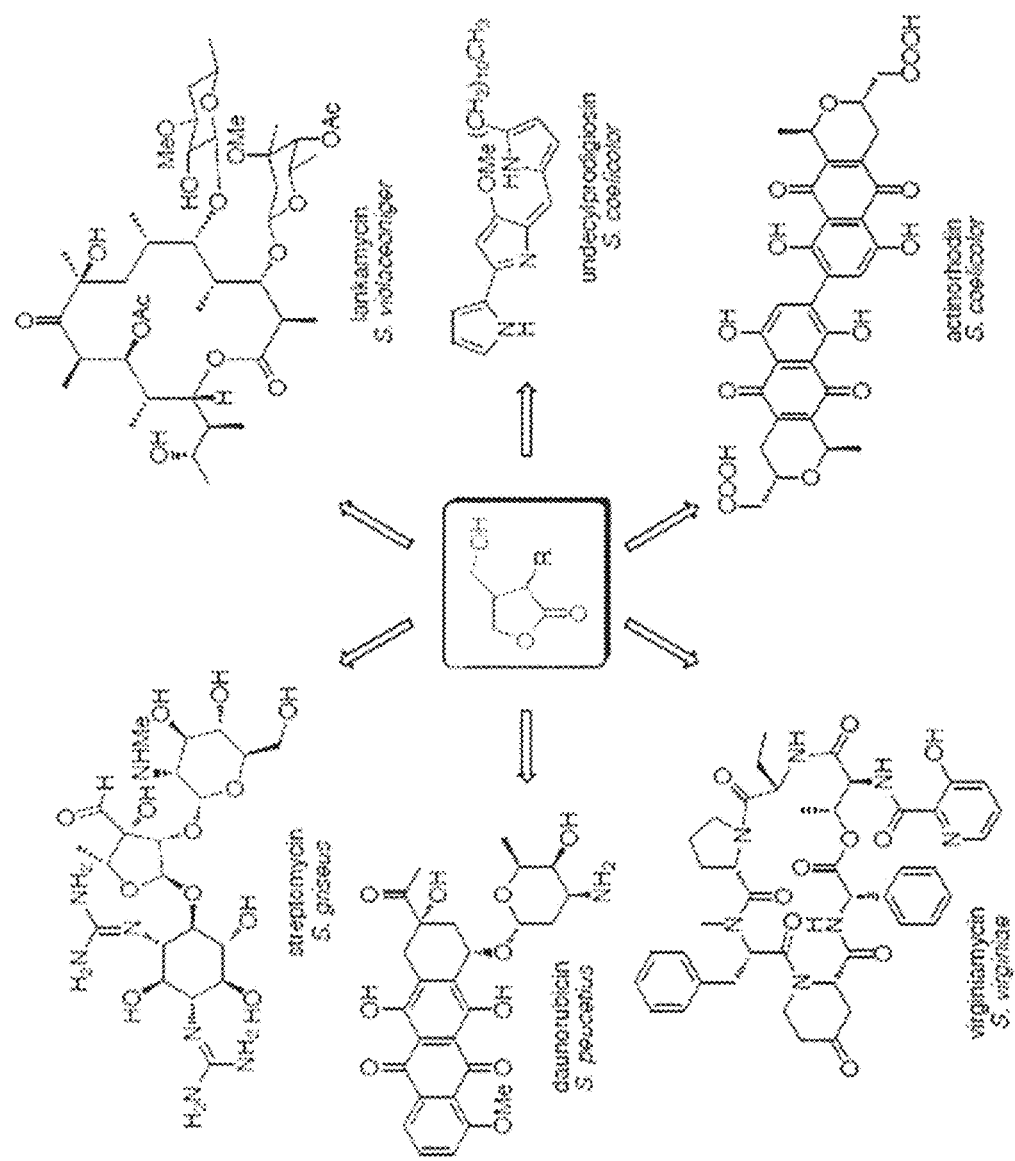
FIG. 4 is an illustration of structures of six antibiotics that are regulated by GBL signaling and the names of the producing strains of *Streptomyces*.

Compositions and methods herein replicate natural environment to activate silent gene pathways in an organism. Small molecules that act as hormones that directly control antibiotic production in *Streptomyces* are synthesized. Only 14 of these naturally occurring hormones have been isolated and classified, the structures of which are shown in FIG. 4.

Signaling hormones such as GBLs were discovered herein that activate secondary metabolic pathways in strains of microorganisms to overexpress production, for compounds the expression of which were previously were considered to be 'silent' or were underexpressed under laboratory conditions, and compounds that previously have not been identified. Rather than attempting to use recombinant nucleic acid cloning techniques isolate, engineer, and re-assemble potential secondary metabolite producing gene clusters, the method herein activates existing pathways in vivo in microorganisms, which at present are underexpressed and are quiescent under physiological conditions absent the GBL.

Various embodiments of the invention herein provide a composition having the formula (VIII or IX):

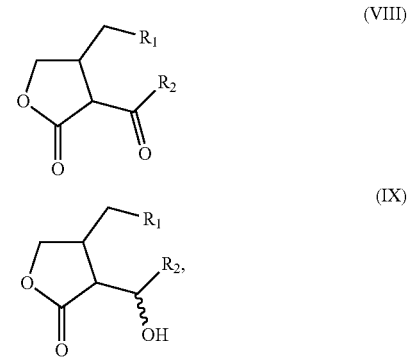

in which $R_1$ is a hydroxyl, hydrogen, optionally substituted alkyl, halogen, cycloalkane, or —C(O)($R_3$). Certain embodiments of the composition herein provide $R_3$ as a hydrogen, optionally substituted alkyl, optionally substituted aryl, or halogen. Certain embodiments of the composition herein provide $R_2$ as a hydrogen, hydroxyl, optionally substituted alkyl, halogen, cycloalkane, or —C(O)($R_4$). Certain embodiments of the composition herein provide $R_4$ as a substituted alkyl, or optionally substituted aryl, halogen, or cycloalkane.

For example, a composition is provided having formula VIII or IX in which $R_1$ is —OH and $R_2$ is methyl, ethyl, n-propyl, n-butyl, n-pentyl, n-hexyl, n-heptyl, or n-octyl. For example, further provided is a composition having formula VIII or IX in which $R_1$ is —OH and $R_2$ is isopropyl, isobutyl, sec-butyl, tetra-butyl, isobutyl, sec-pentyl, isopentyl, isohexyl, 2-methylpentyl, 3-methylpentyl, 2,3-dimethylbutyl, 2,2-dimethyl butyl, 2-methylhexyl, 3-methylhexyl, 2,2-dimethylpentyl, 2,3-dimethylpentyl, 2,4-dimethylpentyl, 3,3,-dimethylpentyl, 3-ethylpentyl, 2,2,4-trimethylbutyl, 2-methylpentyl, 3-methypentyl, 4-methylpentyl, 3-ethylhexyl, 2,2-dimethylhexyl, 2,3-dimethylhexyl, 2,4-dimethylhexyl, 2,5-dimethylhexyl, 3,3-dimethylhexyl, 3,4-dimethylhexyl, 3-ethyl-2-methylpentyl, or 3-ethyl-3-methylpentyl.

Certain embodiments of the composition herein provide $R_2$ as an optionally substituted alkyl chain having a length in a range selected from the group of: one carbon to about eight carbons, one carbon to about 12 carbons, and one carbon to about 20 carbons. In various embodiments of the composition, the optionally substituted alkyl chain contains at one or more positions in the chain a substituent selected from the group consisting of: an alkyl, an aryl, an amino, a hydroxyl, a carbonyl, a halogen, or a sulfur group. Certain embodiments of the composition herein provide the optionally substituted aryl group as an aromatic group such as benzene, pyridine, thiazoles, and the like. In certain embodiments, the optionally substituted aryl groups contain at one or more positions in the ring a substituent selected from the following: alkyl, aryl, amino, hydroxyl, carbonyl, halogens, or sulfur groups.

Various embodiments of the invention herein provide a composition for inducing or upregulating expression of genes involved in biosynthesis of a bioactive microbial product by cells of a strain of a microorganism, the composition including: at least one synthetic non-naturally occurring derivative of a GBL, in a dose effective to increase expression of the genes and biosynthetic production of the product in the cells. The term "synthetic non-naturally occurring" as used herein is defined as a laboratory-produced organic synthesis product, which has a chemical structure different from that of a known endogenously produced GBL found in nature.

For example, the bioactive product has at least one activity selected from the group of: anti-bacterial, anti-fungal, anti-viral, anti-helminthic, anti-spasmodic, anti-cancer, anti-malarial, anti-trypanosomal, complement inhibitory, immune stimulant, anti-inflammatory, immune suppressant, toxin neutralizing, diuretic, and herbicidal.

Figure 5:
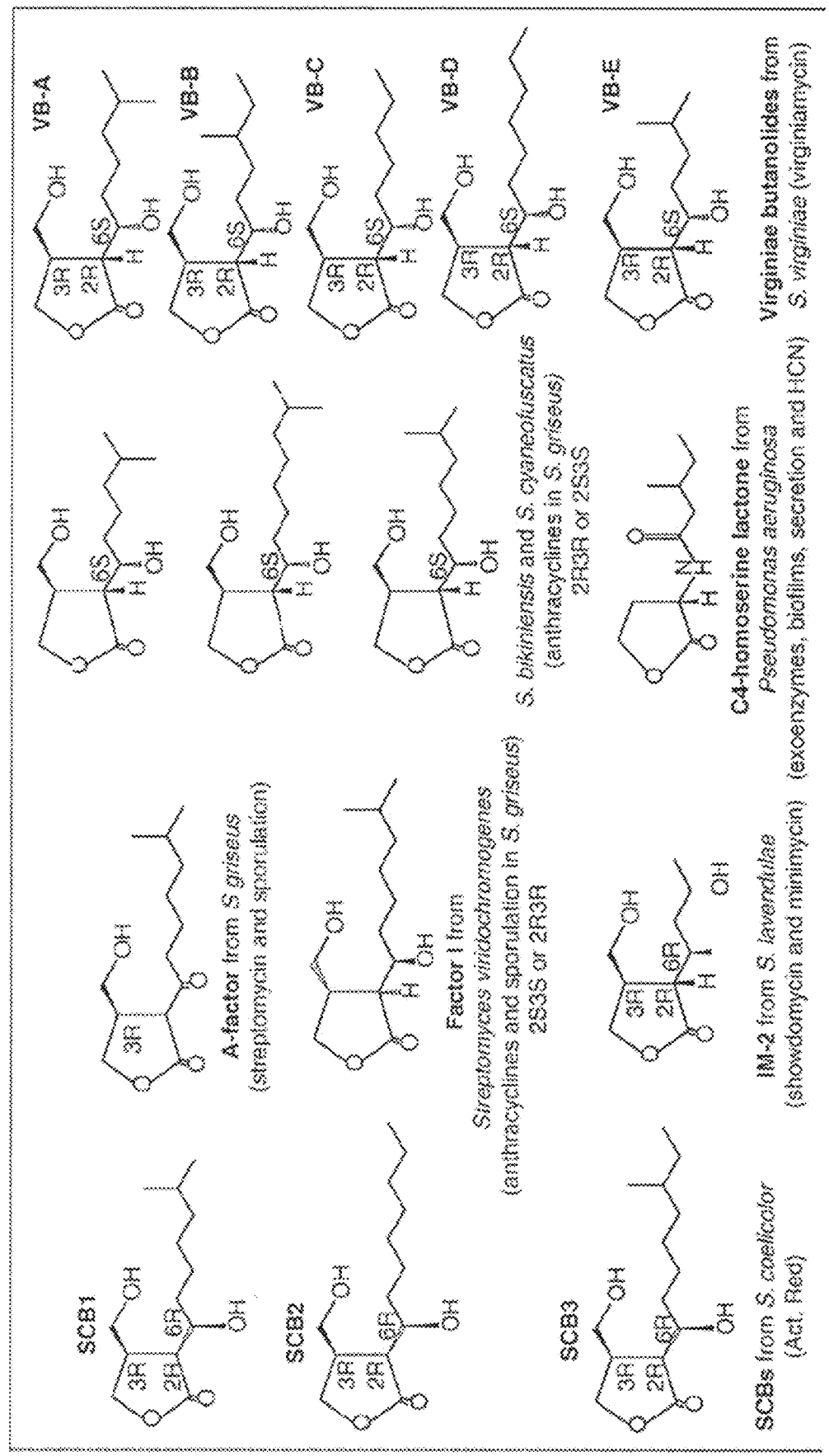
FIG. 5 is an illustration of the structures of 14 known members of the GBL class of signaling molecules that regulate antibiotic production and differentiation, and the names of the cognate species in which production is regulated.

In certain embodiments of the compositions herein, the strain of the microorganism is a mixture of a plurality of strains or species, and the composition is effective to upregulate expression of genes in at least one of the strains or species. Certain embodiments of the composition herein provide that the synthetic non-naturally occurring derivative of the GBL is chemically different from the GBLs listed in FIG. 5, including that the synthetic non-naturally occurring GBLs are different from: S. griseus A-factor; S. viridochromogenes Factor I; S. lavendulae IM-2; S. coelicolor SCB1, SCB2, and SCB3; anthracyclines from S. bikiensis and S. cyaneofuscatus and greater length hydrocarbon chains in 2R3R and 2S3S; and S. virginiae butenolides VB-A, VB-B, VB-C, VB-D, and VB-E. The GBL in embodiments of the composition includes a core substituted at the 3 position by a substituent having the structure methyl-$R_1$ and at the 2 position by a substituent having the structure selected from the group consisting of: ketone-$R_2$, alcohol-$R_2$, carbonyl-$R_2$, such that the substituent at the 2 and 3 position of the GBL are attached to the GBL core by recto (R) or levo (L) bonds, and $R_1$ and $R_2$ are each independently selected from the group consisting of: a lower alkane, an alkyne, an alkoxyl, an alkoxy, a halogen, a sulfide, an amine, a carbonyl, and an alkene selected from the group consisting of: an ethyl, an ethoxy, an ethoxyl, a propyl, a propoxy, a propoxyl, a butyl, a pentyl, a hexyl, a t-butyl, an s-butyl, an i-butyl, an i-pentyl, an i-hexyl, and an i-heptyl.

Certain embodiments of the compositions have the GBL core substituted at the 2 or 3 position with a lower alkane having a length of one carbon to about eight carbons.

Alternatively, in embodiments of the composition, the GBL core is substituted at the 2 or 3 position with an alkane having a length greater than eight carbons. For example, embodiments of the composition provide GBLs that have a chemical structural formula from the group consisting of molecules having the formulas I-VII in FIG. 10. Certain embodiments of the compositions here provide that the $R_1$ is a hydroxyl and is either recto-(R) or levo-(L), and $R_2$ is a hexyl substituent which is R or L.

An embodiment of the invention herein provides a method of improving a yield of a microbially-produced bioactive secondary metabolite product, the method including contacting cells of a strain of microorganism with a suitable amount of at least one GBL composition in which the GBL is non-cognate to the strain or is synthetic and non-naturally occurring, and culturing the cells of the strain with the GBL under conditions for production of the product; and, obtaining the product from the cell fermentation culture by separation of cells and medium or purification of the product from the cells and analyzing the amount of the product, such that the yield of the product per unit of volume of culture or weight of cells is greater than that from control cells of the strain not contacted with the GBL composition and otherwise identically cultured and analyzed, such that the yield of the product from the cells cultured with the derivative of the GBL is improved compared to that from the control cells.

The strain of the microorganism is generally bacterial, fungal, or algal. For example, the strain of microorganism is bacterial and is an actinomycete. For example, the actinomycete is a genus selected from the group of genera consisting of: *Actinopolyspora, Amycolatopsis, Micromonospora Nocardia, Pseudonocardia, Saccharothrix, Saccharopolyspora, Salinospora, Streptomyces, Tetinomedara*, and *Verrucosispora*. In a further example, the actinomycete is at least one streptomycete selected from the group of: *Streptomyces avermitilis, S. aureofaciens, S. capreolus, S. cattleya, S. clavuligerus, S. coelicolor, S. fradiae, S. garyphallus, S. griseus, S. kanamyceticus, S. levoris, S. lincolnensis, S. niveus, S. noursei, S. platensis, S. plicatus, S. pristinaespiralis, S. orientalis, S. ribosidifus, S. rimosus, S. roseosporus, S. scabiei, S. venezuelae, S. vinaceus*, and *S. virginiae*; or is at least one *Pseudonocardia* selected from the group of: *P. acacia; P. ailaonensis; P. adelaidensis; P. alaniniphila; P. ammonioxydans; P. carboxydivorans; P. halophobia; P. kujensis; P. nitrificans; P. petroleophila; P. salamisensis; P. sulfoxidans; P. thermophila*; and *P. zigingensis*; or is at least one *Amycolatopsis* selected from the group of: *A. alba, A. azurea, S. balhimycena, A. coloradensis, A. fastidiosa, A. keratiniphila, A. lurida, A. mediterranei, A. orientalis, A. sulphurea, A. tolypomycina*, and *A. vancoresmycina*.

Figure 10:
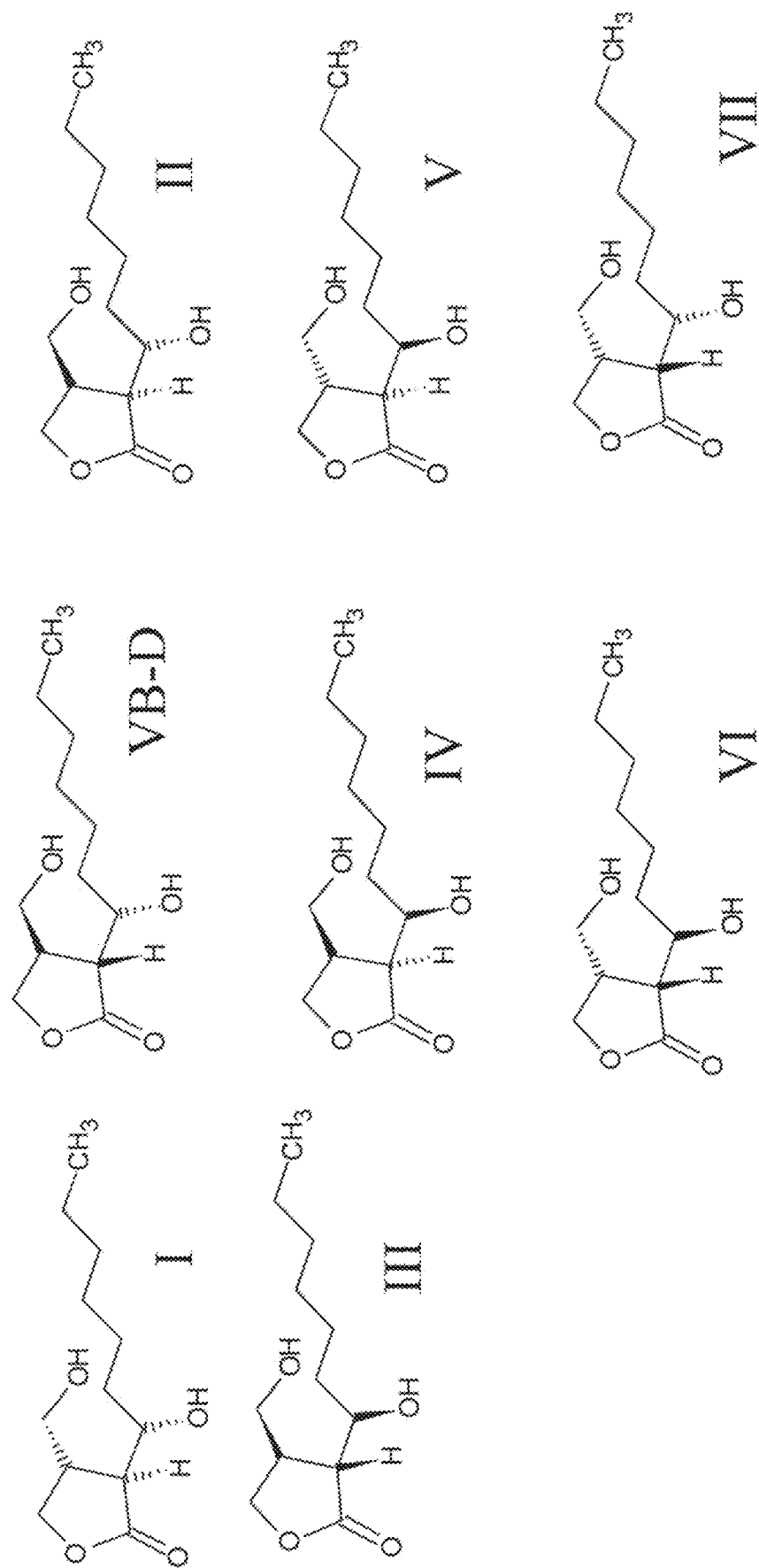
FIG. 10 is an illustration of the structures of non-naturally occurring enantiomeric GBLs named herein as 1-VII, and the structure of naturally occurring VB-D.

An embodiment of the method includes a derivative of the GBL that is synthetic and non-naturally occurring and is at least one of the compositions selected from formulas I-VII in FIG. 10. Embodiments of the method result in the yield from the cells contacted with the GBL having at least about two-fold great, four-fold great, ten-fold greater, twenty-fold, fifty-fold, or hundred-fold greater than the yield from the control cells.

Embodiments of the invention herein provide a method of discovery of a cell-produced secondary metabolic compound in a microbial strain containing putative unexpressed or under expressed genes encoding enzymes for biosynthesis of a chemical entity having a medicinal or industrial biological activity, the method including: contacting at least one cell sample or a plurality of cell samples, the samples containing mixtures of cells from a plurality of microbial strains with a suitable amount of at least one synthetic GBL in which the microbial strains are selected from the group of: fresh isolates from nature, naturally occurring mixtures of unpurified microorganisms, and an established species strain such that the GBL and the established species are non-cognate; culturing the cell samples with the GBL derivative under conditions for production of secondary metabolite chemical compounds; screening the cultures by at least one detection system for presence of the biological activity, such that the presence of the activity identifies the producing sample containing at least one strain of microorganism producing the chemical having the activity; and, characterizing at least one chemical structure having the biological activity, and comparing the structure to a library database of known chemical entities to obtain chemicals not previously known, thereby screening to discover the chemical compounds with the biological activity.

"Synthetic" as used herein is defined as a laboratory-produced organic synthesis product, which has a chemical structure that either is naturally occurring or non-naturally occurring. "Non-cognate" as used herein is defined as a signaling molecule, such as a GBL, that is exogenously supplied to the microorganism and is not known at the time of the current application to be endogenously produced by that microorganism, or at the time that microorganism is screened in the presence of the signaling molecule using the methods herein. "Non-naturally occurring" a used herein is defined as haing a chemical formula and/or a steric configuration not know to be produced by an organism found in nature.

1. Certain embodiments of the method herein provide that the method further include, prior to screening, mixing cells to obtain the samples of the plurality, such that each sample of the at least one or the plurality contains at least two, at least five, or at least 10 strains. Certain embodiments of the method provided herein, the GBL is a plurality of GBLs each having a different chemical structure. For example, at least one or the plurality includes at least one, at least two, at least four, at least five, or at least ten GBLs, each having a different chemical structure. The different chemical structure includes GBLs that are racemates or a racemic mixture, and racemates include those that are non-naturally occurring. In embodiments of the method herein, the screening further includes contacting each of the samples to the detection system which is an assay including at least one component selected from the group of: an organism, a tissue, a cell culture, and an enzyme of a detection system; and measuring an activity selected from: anti-bacterial, anti-fungal, anti-viral, anti-helminthic, anti-cancer, anti-malarial, anti-trypanosomal, complement inhibitory, immune stimulant, anti-inflammatory, immune suppressant, toxin neutralizing, diuretic, and herbicidal.

In embodiments of the culturing step, growing the cells of the strain of microorganism identified as producing the chemical is performed in a liquid medium, and the method further includes prior to screening, separating the cells from the medium to obtain a resulting supernatant depleted of the cells. Alternatively, culturing is growing the cells of the strain of microorganism in contact with soil. In embodiments of the method herein, the method further includes prior to screening, separating the cells from the soil and washing the soil and cells, to obtain a resulting supernatant enriched for extracellular products.

An embodiment of the method herein provides after identifying, isolating the chemical compound from the producing culture contacted with the GBL. The method further may include isolating the at least one GBL from the plurality of GBLs contacted to the sample that induces expression of the product. The method provides characterizing the chemical structure and analyzing by at least one method selected from the group consisting of: mass spectrometry (MS), gas chromatography, thin layer chromatography, matrix-assisted laser desorption/ionization (MALDI), MALDI-time of flight (MALDI-TOF), moving bed chromatography, and high performance liquid chromatography (HPLC). Embodiments of the method herein provide culturing alternatively, as growth of the strain or strains on solid medium. Using solid medium, screening further includes adding cells of a target indicator strain including at least one of a bacterium, a fungus, a eukaryotic cell, a white blood cell, and a eukaryotic tissue explant. The method further includes testing a sample of the supernatant from a liquid culture in a test subject which is an experimental animal model of a disease. The method alternatively provides a further step of testing a sample of the supernatant in vivo in cultured cells or tissues of a mammal, a plant, or an insect.

Embodiments of the method herein provide a further step of obtaining coordinates of peaks observed by MS, MALDI, MALDI-TOF, or HPLC corresponding to presence of the secondary metabolism products of the strain of the microorganism, and comparing the location of the peaks to that of known previously characterized products to identify novel chemical entities. Certain embodiments of the method herein provide a step of screening separately each of the plurality component strains for production of the novel chemical entities, to identify which strain produces the novel entity. Such a method was used herein to obtain induction of synthesis of a potentially novel compound from a culture of *S. coelicolor* having characteristics different from those in a database library, and eluting in a peak at 1.84 by liquid chromatography.

Various embodiments of the invention herein provide a method of increasing or accelerating production of a microbial secondary metabolism compound, the method including: contacting a culture of a producing microorganism strain with a GBL at an effective dose to upregulate expression of genes encoding enzymes that synthesize the compound, in which the GBL is non-cognate to the strain. The non-cognate GBL is, for example, synthetic and non-naturally occurring, or is not native and not endogenously made by the producing microorganism strain.

In alternative embodiments of the method herein, the GBL is added at or before inoculation of production culture medium with the microorganism; or the GBL is added after inoculation, or during growth of the cells of the strain; or the GBL is added at stationary phase or after cessation of growth of the cells of the strain; or the GBL is added at a plurality of time points during culture of the micro-organism.

Various embodiments of the invention herein provide a method of organic synthesis of a GBL having a formula of:

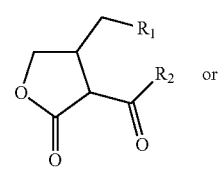

(VIII)

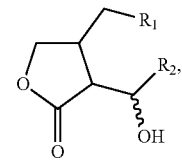

(IX)

the method including: acylating 2,2-dimethyl-1,3-dioxane-4,6-dione (Meldrum's acid) in a mixture of a pyridine and anhydrous dichloromethane ($CH_2Cl_2$), and esterifying the acylated 2,2-dimethyl-1,3-dioxane-4,6-dione with a mono-TBDMS (tert-butyldimethylsilyl) protected dihydroxyacetone to form a beta-keto-ester and mixing with toluene and heating a resulting mixture; condensing the heated mixture of the beta-keto-ester and the toluene with an excess of silica under conditions in which a Knoevenagel condensation results in a protected butenolide bound to the silica at room temperature and purifying by further silica using a column to elute the protected butenolide; and reducing the butenolide with sodium cyanoborohydride to form a 2,3 di-substituted gamma-butyrolactone, and deprotecting the 2,3 di-substituted GBL at room temperature to form the GBL having the formula of VIII or IX.

In various embodiments of the method, $R_1$ is provided as at least one moiety selected from the group consisting of a hydroxyl, a hydrogen, an optionally substituted alkyl, a halogen, a cycloalkane, and a —$C(O)(R_3)$. Further, $R_3$ is at least one selected from the group of a hydrogen, an optionally substituted alkyl, an optionally substituted aryl, and a halogen. Further, $R_2$ is at least one selected from a hydrogen, a hydroxyl, an optionally substituted alkyl, a halogen, a cycloalkane, and a —$C(OXR_4)$. $R_4$ is at least one selected from the group consisting of: a substituted alkyl, an optionally substituted aryl, a halogen, and a cycloalkane. For example, the optionally substituted alkyl chain contains at least 8 carbon atoms, at least 12 carbon atoms, or at least 20 carbon atoms. For example, the optionally substituted alkyl is substituted at one or more carbons in the chain with at least one substituent selected from an alkyl, an aryl, an amino, a hydroxyl, a carbonyl, a halogens, and a sulfur group. For example, the optionally substituted aryl is an aromatic moiety selected from the group consisting of: benzene, pyridine, and thiazoles. For example, the optionally substituted aryl is substituted at one or more positions in the ring with at least one substituent selected from the group consisting of: an alkyl, an aryl, an amino, a hydroxyl, a carbonyl, a halogen, and a sulfur.

Various embodiments of the invention herein provide a method of organic synthesis of a GBL including acylating 2,2-dimethyl-1,3-dioxane-4,6-dione (Meldrum's acid) in a mixture of a pyridine and anhydrous dichloromethane ($CH_2Cl_2$); esterifying the acylated 2,2-dimethyl-1,3-dioxane-4,6-dione with a mono-TBDMS (tert-butyldimethylsilyl) protected dihydroxyacetone to form a beta-keto-ester, and reducing the butenolide with sodium cyanoborohydride to form a 2,3 di-substituted GBL; and deprotecting the 2,3 di-substituted GBL at room temperature to form with an improvement including, prior to deprotecting: mixing the beta-keto-ester with toluene and heating a resulting mixture on silica; and condensing the heated mixture of the beta-keto-ester and the toluene with silica, prior to purifying, under conditions in which a Knoevenagal condensation results in a protected butenolide bound to the silica at room temperature, resulting in obtaining an improved yield and a quicker reaction. For example, the reaction yields a butenolide in about two to three hours.

Certain embodiments of the method herein provide the step of, prior to esterifying acylated Meldrum's acid, combining dichloromethane and a catalyst that is 1-methylimidazole to form mono-TBDMS (tert-butyldimethylsilyl) protected dihydroxyacetone.

Example 1—Acylation of Meldrum's Acid as a Step of Organic Synthesis of GBLs

Hormones that are novel because they are not found in nature are synthesized using organic chemistry methods herein. The non-naturally occurring hormones were contacted to cells of *Streptomyces* species to determine antibiotic production, as visualized by the induction of the pigmented antibiotic actinorhodin or some other detection assay. The hormones synthesized and analyzed herein were not native to *S. coelicolor*, viz., the hormones are not endogenously produced and hence are non-cognate with respect to this species. GBL signaling molecules used herein include, but are not limited to, VB-C, VB-D, and A-Factor.

Figure 6:
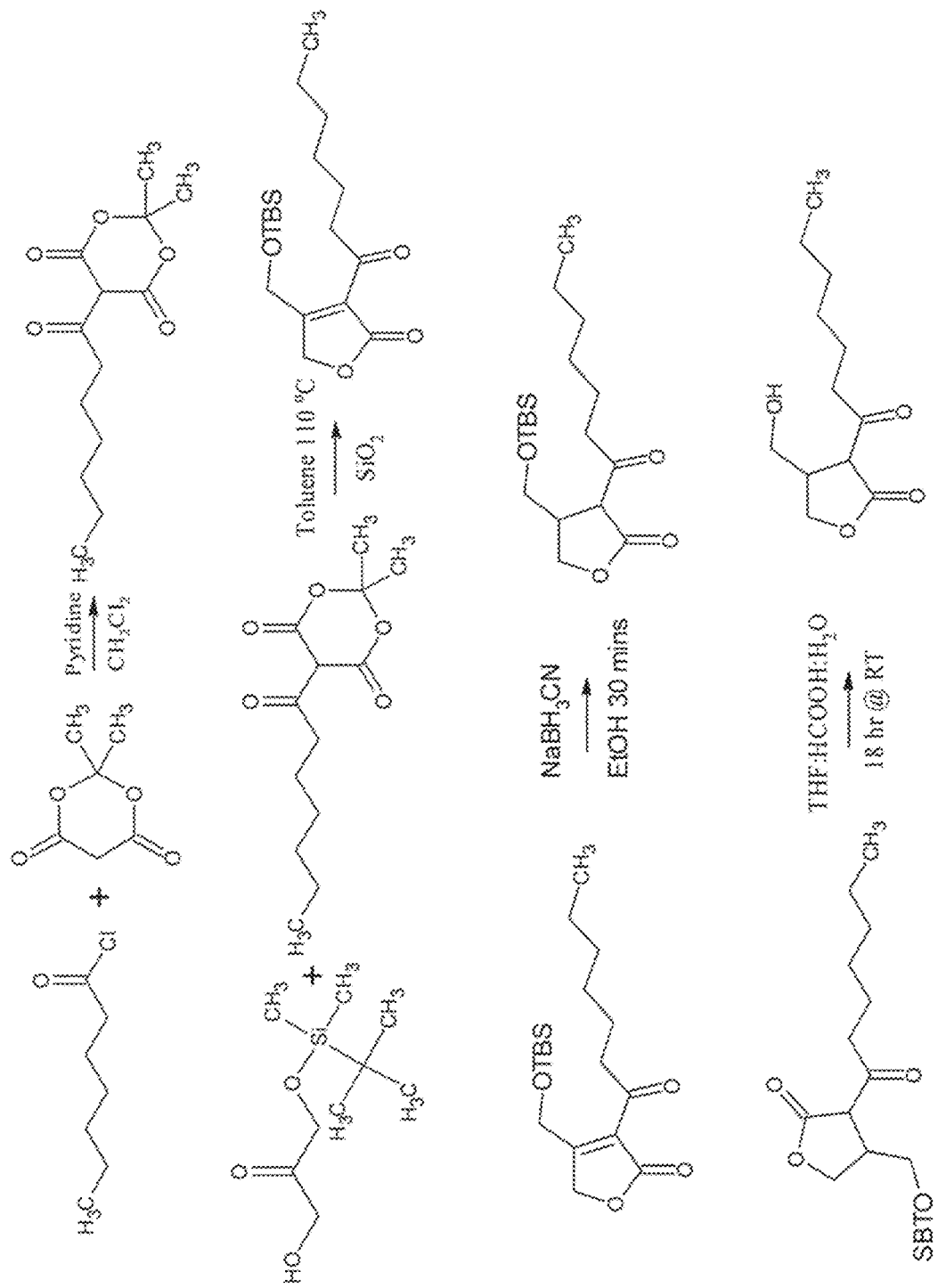
FIG. 6 is an illustration of the organic synthesis of the GBLs of the compositions and methods herein.

The organic synthesis of a GBL is shown in FIG. 6. Meldrum's acid was acylated with acyl-halides yielding a diverse number of analogues. To acylate Meldrum's acid, a 250 mL round bottom flask was charged with 17.76 g (0.123 mol) recrystallized Meldrum's acid (2,2-dimethyl-1,3-dioxane-4,6-dione). A stir bar and 65 mL anhydrous dichloromethane was added to the flask. The flask and its contents were cooled in an ice bath. Anhydrous pyridine, 24.3 mL (0.30 mol), was added dropwise to the Meldrum's acid over a 10 minute period. Meldrum's acid was combined with other reagents in parts because the acid decomposes at the higher temperatures. Heptanoyl chloride, 19.04 mL (18.27 g/0.123 mol), was added drop-wise over a 2 hour period to the clear solution in 50 mL anhydrous dichloromethane. After the 2 hour addition period, the reaction was stirred on ice for 1 hour, then brought to room temperature and stirred for an additional 1 hour. Yields of acylated Meldrum's acid were surprisingly greater than 90% using heptanoyl chloride in DCM dried over $NaSO_4$, and without the use of a nitrogen atmosphere. See, Organic Syntheses, Coll. Vol. 7, p. 359 (1990); Vol. 63, p. 198 (1985).

The reaction mixture was diluted with an additional 50 mL dichloromethane, then washed twice with 50 mL partitions of 2N HCl. The aqueous phase was extracted three times with dichlormethane, and the organic phases pooled, washed once with saturated NaCl, and dried over anhydrous sodium sulfate. Dichlormethane was removed with rotary evaporation to yield a pale yellow/deep red/orange oil or solid as a product.

Example 2—Alternative Synthesis Procedures for Acylation of Meldrum's Acid

Recrystallized Meldrum's acid is added to a round bottom flask of an appropriate size. An organic solvent such as hexane, dichlormethane, chloroform, heptane, toluene, dichloroethane, or cyclohexane, was added to the flask. The flask and its contents are cooled in an ice bath. A 2.5 mol equivalent of anhydrous pyridine was added dropwise to the Meldrum's acid over a period of time of either 5 seconds, 30 seconds, 5 minutes, 10 minutes, 30 minutes, 60 minutes, or 24 hours. A solution of an acyl-halide at a molar ratio of 0.005, 0.010, 0.150, 1, 2, 3, 5, or 10 was added to the clear solution of Meldrum's acid and catalyst over a period of 5 seconds, 30 seconds, 5 minutes, 10 minutes, 30 minutes, 1 hour, 2 hours, 5 hours, 10 hours, or 24 hours.

Figure 15:
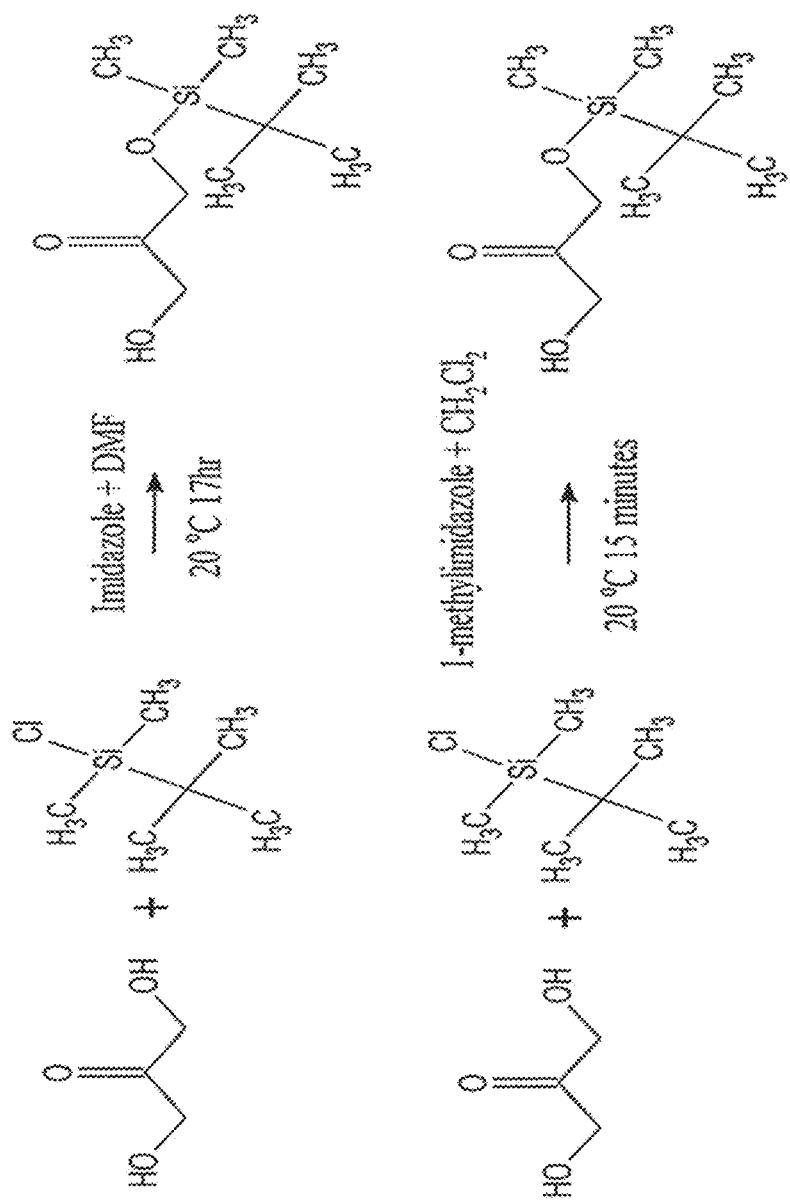
FIG. 15 is an illustration of the organic synthesis reaction of mono-silylated dihydroxyacetone (DHA) used herein.

Example 3—Deprotection and Esterification Techniques to Provide Improved Reaction Time and Yield Reactions forming mono-silylated dihydroxyacetone (DHA) are shown in FIG. 15. The protection reaction shown at the top of the figure using imidazole and DMF yields di-protected, mono-protected, and the tert-butyldimethylsilyl ether (TBDMS). DMF removal is challenging using this method, and the deprotecting reaction runs overnight. Methods provided herein were devised to replace the catalyst imidazole with 1-methylimidazole, and the results reduced reaction time from 17 hours to 15-20 minutes. The recovery for reactions using 1-methylimidazole as a catalyst was about 50%.

Esterification of the crude reaction containing TBDMS-DHA and acylated Meldrum's acid yielded a crude reaction of uncyclized ester and butenolide. Mono-protected DHA species protected with a TBDMS group was reacted with acylated Meldrum's acid species to yield beta-keto-ester. Immediately following consumption of mono-DHA, the reaction was stopped and combined with 110° C. toluene. While still hot, the mixture was poured over a small amount of silica in a beaker (1 g crude reaction to 2 g silica) to form β-keto-ester. This mixture was reacted for one hour and then stored at −20° C. overnight.

Beta-keto-ester was formed as hot reaction mixture was heated on a mixture of silica for about an hour to improve the cyclization of the ester into the butenolide. Beta-keto-ester was cyclized into substituted butenolide in about 10-15 minutes. Alternatively, it is envisioned that dimethylformamide and imidazole are substituted in place of dichlormethane and 1-methylimidazole. After butenolide formation, the mixture was loaded onto a silica column for purification.

In an alternative method, the crude reaction is loaded directly onto a column containing four times excess of silica for purification, and the column is incubated and sits overnight. See, Morin et al., *Organic and Biomolecular Chemistry*, 10: 1517-20. PMID: 22246070 (2012).

Figure 14A:
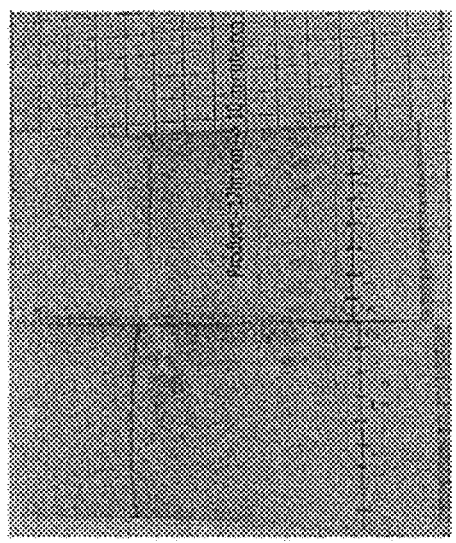
FIG. 14 A-C are photographs of thin-layer chromatograms (TLC) comparing results of the butenolide formation step shown in FIG. 6 to the results of the reaction conducted using an organic synthesis method of Morin et al., *Organic and Biomolecular Chemistry*, 10: 1517-20. PMID: 22246070 (2012).
Figure 14C:
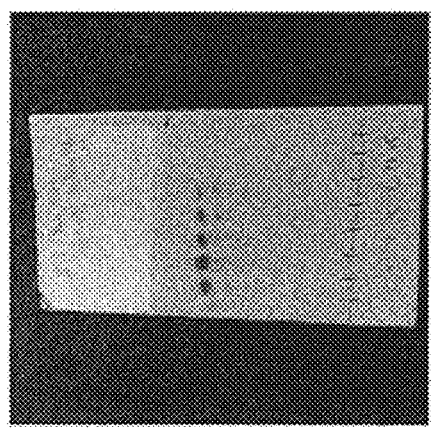
Figure 14B:
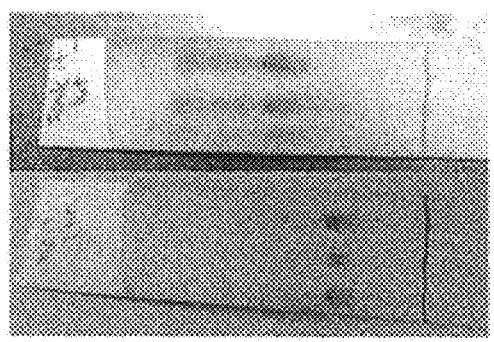

The photographs of TLC results in FIG. 14A-14C show the complete disappearance of the purple ester and full formation of blue butenolide, which indicates an improved yield for the synthesis method used herein.

The traditional method of butenolide formation is a "spontaneous" reaction with a low yield as evidenced by the purple spots at the bottom of the chromatogram in FIG. 14A. The chromatogram of FIG. 14B comparison of the traditional method yield with the modification indicates that the traditional method results in a high volume of products and a low yield of butenolide.

Greater energy was entered into the reaction performed herein by further heating the reaction mixture prior to combining with silica, which may have improved efficiency in the presence of the Lewis Acid catalyst (the silica gel), as shown the presence of blue spots and fewer purple spots in FIG. 14B. Allowing the mixture to remain on silica overnight was observed to result in nearly complete cyclization of ester into a butenolide as shown by an increase in blue spots and lack of purple spots in FIG. 14C.

Figure 11:
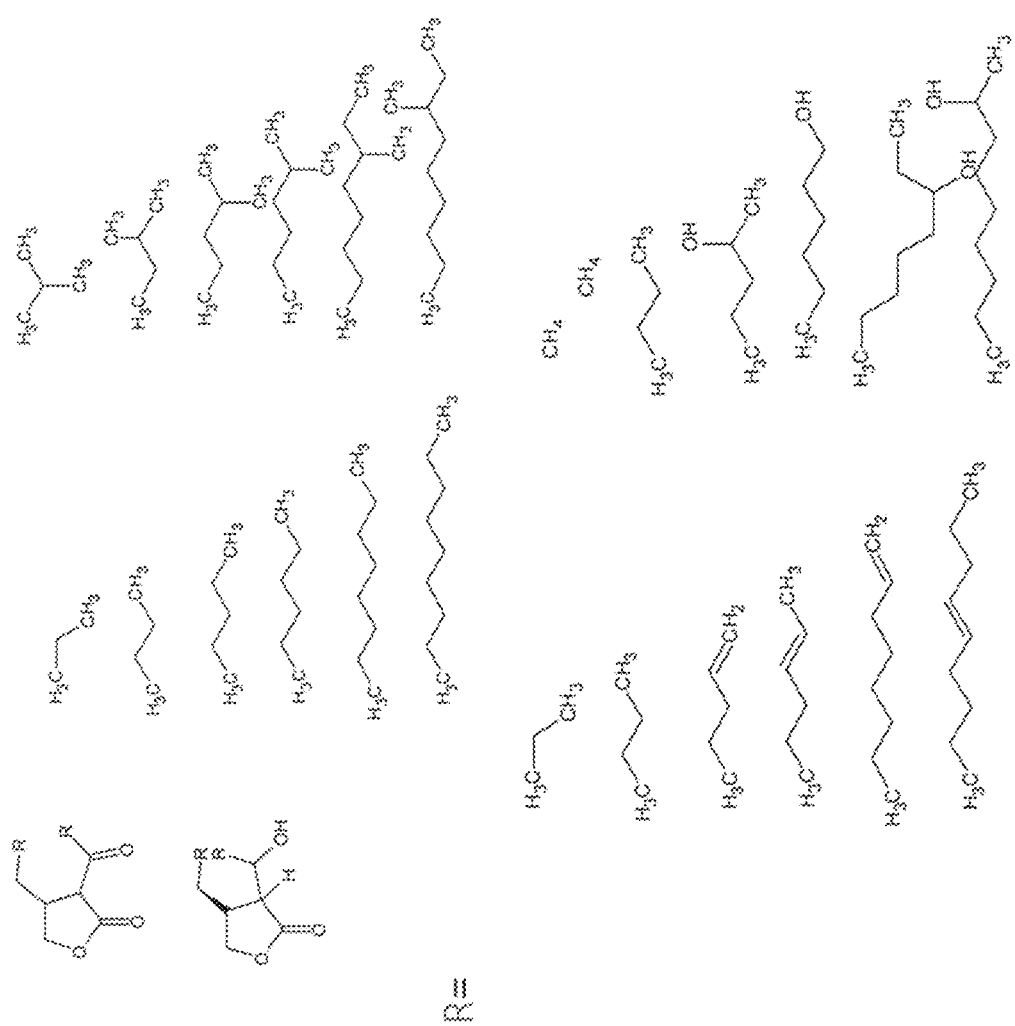
FIG. 11 is an illustration of the structures of potential functional groups to use to synthesize novel GBL derivatives to screen to determine activity to induce antibiotic production.
Figure 13:
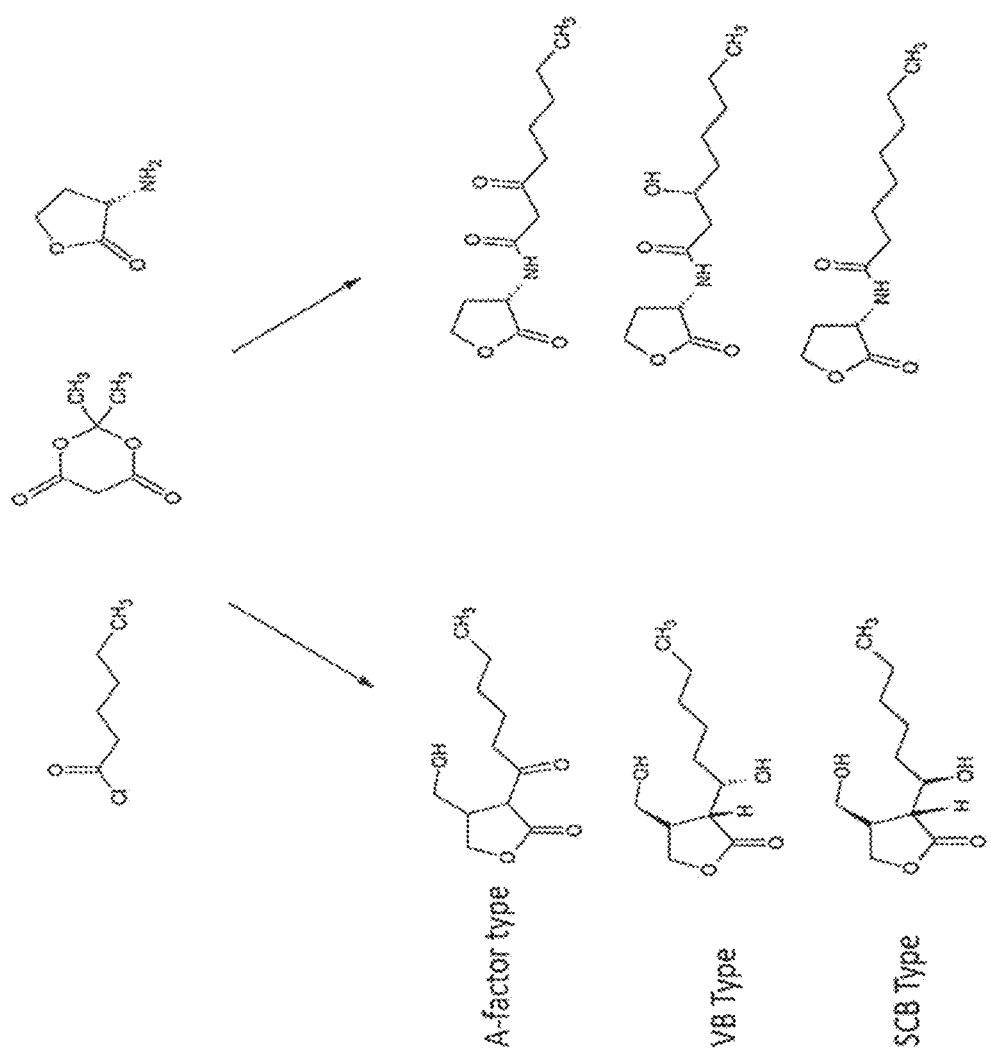
FIG. 13 is an illustration non-naturally occurring analogs of A-factor type, VB type, and SCB type of GBLs and acylated homoserine lactones (AHLs) for synthesis and testing for activity to induce antibiotic production.

After the butenolide was formed, reduction was necessary to yield the GBL. Sodium cyanoborohydride in ethanol was used, which reduced the butenolide within 30 minutes. Because excessive reduction may occur at the ketone yielding an alcohol, the reaction was monitored and quenched. Excessive reduction provides access to the VB type and IM type GBLs. After reduction, deprotection was performed to yield a racemic mixture of 2, 3-disubstituted GBL species having formulas VIII and IX. It is envisioned that the non-naturally occurring GBLs may have at least one of the function group modifications in FIG. 11. For example, analogs of A-factor type, VB type, and SCB type of GBLs that can be synthesized and tested for activity to induce antibiotic production, as shown in FIG. 13.

Example 4—Use of a Racemic Mixture of GBLs to Screen for Antibiotic Production

Figure 9:
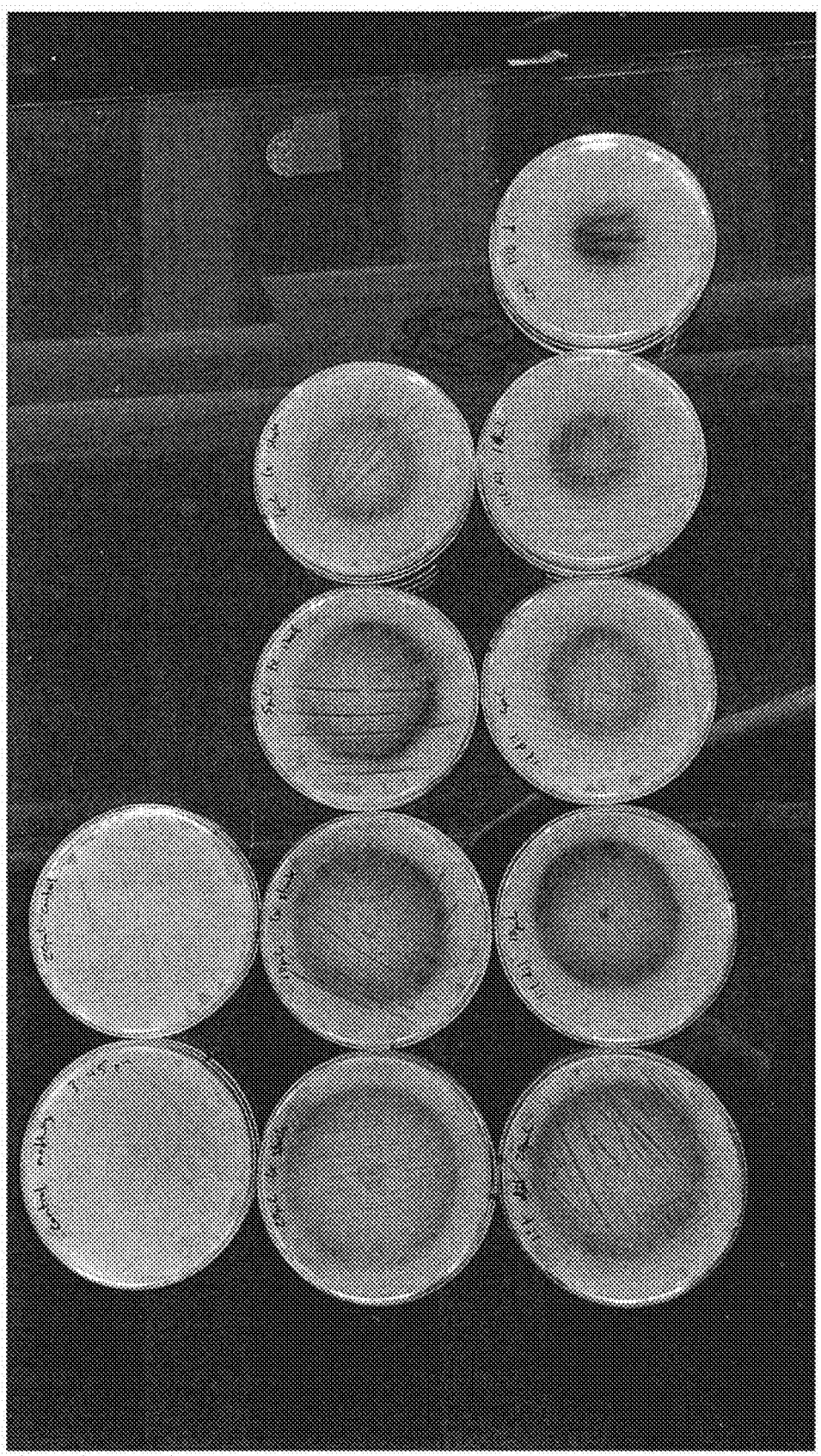
FIG. 9 is a photograph of control plate cultures (top row) of *S. coelicolor* contacted with vehicle, and experimental plate cultures of *S. coelicolor* contacted with a racemic mixture of VB-D and seven enantiomer GBLs thereof having the formulas I-VII (see, FIG. 10). The dark area on the plates indicates production of the blue antibiotic, actinorhodin, and red prodiginies. A monotonic dose-dependent response of antibiotic production (diameter of dark spot) as a function of amount of GBL mixture was observed.

The formulas I-VII in FIG. 10 illustrate the structures of the enantiomers in the mixture of GBLs tested for ability to elicit antibiotic production, the results of which are shown in the plates in FIG. 9. Each GBL has the same gross chemical formula with different chirality at asymmetric carbons, hence have different three-dimensional structures and are enantiomers. The mixture of GBLs was added to a pure culture of non-cognate microorganism *S. coelicolor*. Streptomycete strains were cultured in complex medium R5 or in minimal medium MMS. See Kieser, T. et al., Practical *Streptomyces* Genetics, John Innes Institute, 2000. Data obtained show that production of an antibacterial activity was elicited, which are the dark circles (pigmented secondary metabolites) produced on solid medium and which was found to be produced as a function of the amount of the GBLs deposited per plate.

Racemic mixtures of enantiomers were contemplated to be more efficient from a testing standpoint because multiple biologically active GBLs could be tested in a single assay, so that the assay is a multiplex test of the eight enantiomers. VB-D is a naturally occurring GBL of *S. virginiae*, and is non-cognate to *S. coelicolor*, which was used as a test strain of microorganism to determine effect on antibiotic production. This species is known to produce a purple antibiotic, actinorhodin, production of which is used as a model system for studies of regulation of antibiotic biosynthesis. The dark areas in the plates in FIG. 9 results from production of the purple antibiotic actinorhodin.

Spore stock of *S. coelicolor* was used to inoculate SMMS agar (solid SMM medium) and the spore suspension on the surfaces of the plates was allowed to dry. The GBL amounts were added at the time of inoculation. No antibiotic production was observed on the plates after 24 only hours.

The two plates in the top of the photograph of FIG. 9 are controls cultures of *S. coelicolor*. The control plate on the left is a negative control in which no GBL nor vehicle was added. The control plate on the right was contacted with the vehicle only, which was a mixture of methanol and water.

A racemic mixture of GBLs containing the non-naturally occurring compounds 1-VII and *virginiae* butenolide-D (VB-D) was synthesized, and an amount of about 500 μg was dissolved in 100 μL of vehicle to yield a 5 mg/ml concentration solution. The plates of the second row from left to right were spotted with 20 μL (100 μg), 10 μL (50 μg), 5 μL (25 μg), and 1 μL (5 μg) of the 10 mg/ml concentration solution, respectively. The first four plates from left to right of the third row were spotted with 20 μL (50 μg), 10 μL (25 μg), 5 μL (12.5 μg), and 1 μL (2.5 μg) of a 1:2 dilution of the 10 mg/ml concentration solution which had a 2.5 mg/mL concentration, respectively. The fifth plate of the third row was spotted with 2 μL (1 μg) of a 1:10 dilution of the 10 mg/ml concentration solution. It was observed after 42 hours that each of the experimental plates produced antibiotic evidenced by the dark spot and the production was dose-dependent monotonically on amount of GBL.

Example 5—Bacterial Culture

*Streptomyces* species used in methods herein were altered and tested using the methods provided in Hopwood et al., *Genetic Manipulation of Streptomyces a Laboratory Manual* (1985), which is hereby incorporated by reference in its entirety. Further, this reference provides culture techniques, media preparation, temperature and additional culture conditions, recombinant production and manipulation of *Streptomyces* species. Additional media are described in Kieser, T. et al., Ibid. Special culture conditions of media and temperature for spore production in various strains are well-known in the art and are indicated by species for bacteria in *Bergey's Manual of Systematic Bacteriology*, Vol. 1-5 (2001-2012), New York, N.Y., Springer-Verlag. See also, Difco Manual, 2$^{nd}$ Ed. 1009, B-D, Sparks, M.D.

Microorganisms were contacted or treated with natural, cognate, non-cognate, and synthetic non-signaling hormones that activate and/or overexpress gene clusters responsible for secondary metabolite synthesis in the cells. Methods are provided herein for discovery and design of GBL-like compounds that improve yields of antibiotics produced by microorganisms. For example, the microorganism is a strain of bacteria, fungi, protozoa, viruses, or microalgae, which is a non-limiting list. Previously unknown bioactive compounds from known and unknown microorganism strains of species are discovered by methods herein. Environments are sampled to screen for producing strains, the environments including but not limited to, fresh water sediment, seawater sediment, soils such as from forest, farmland, tundra, alpine region, or landfill. Special media may include sterile or fresh environmental components. See, Lewis K. et al., *Nature Reviews Drug Discovery* 12: 371-387 (2013).

Figure 8:
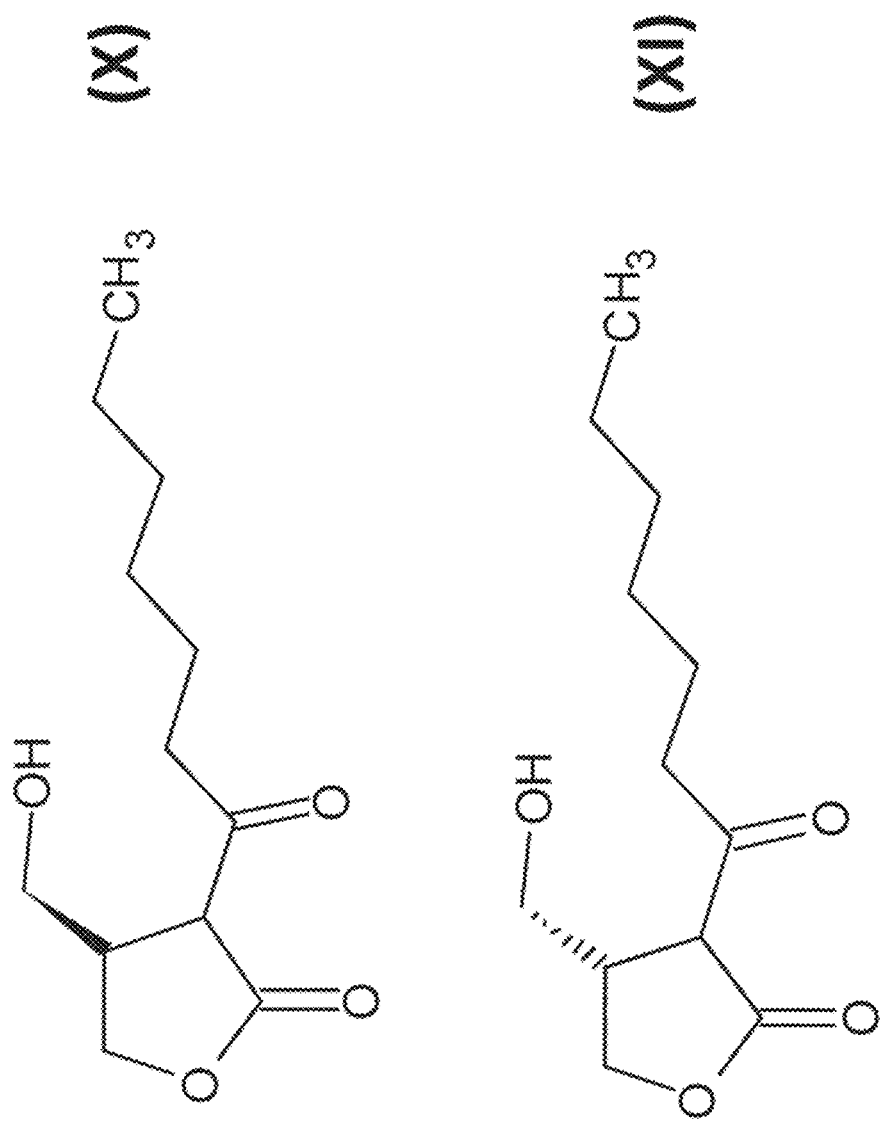
FIG. 8 is a drawing of the structures of non-naturally occurring GBLs and indicated herein as X and XI.

Example 6—Non-Cognate GBL Induction of Antibiotic Biosynthesis in *S. coelicolor* by Non-Naturally Occurring Synthetic GBLs Two non-naturally occurring GBLs designed and synthesized by the methods herein have a formula of X and XI, respectively, and are shown in FIG. 8. These GBLs were analyzed for ability to increase antibiotic production in *S. coelicolor*.

Figure 3:
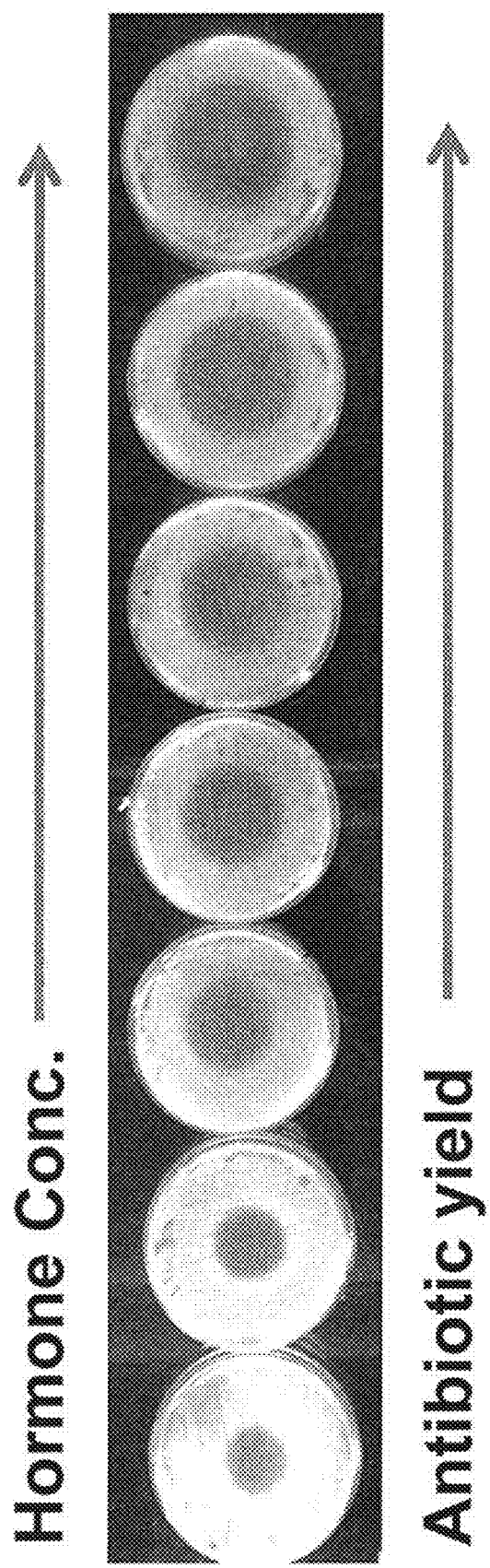
FIG. 3 is a photograph of culture plates containing *S. coelicolor* as in FIG. 2 arranged as a function of increasing amount of GBL contacted to each plate from left to right showing actinorhodin production. The figure shows a dose-dependent increase in antibiotic production from *S. coelicolor* in response to increased GBL concentration contacted on the successive plates.
Figure 7:
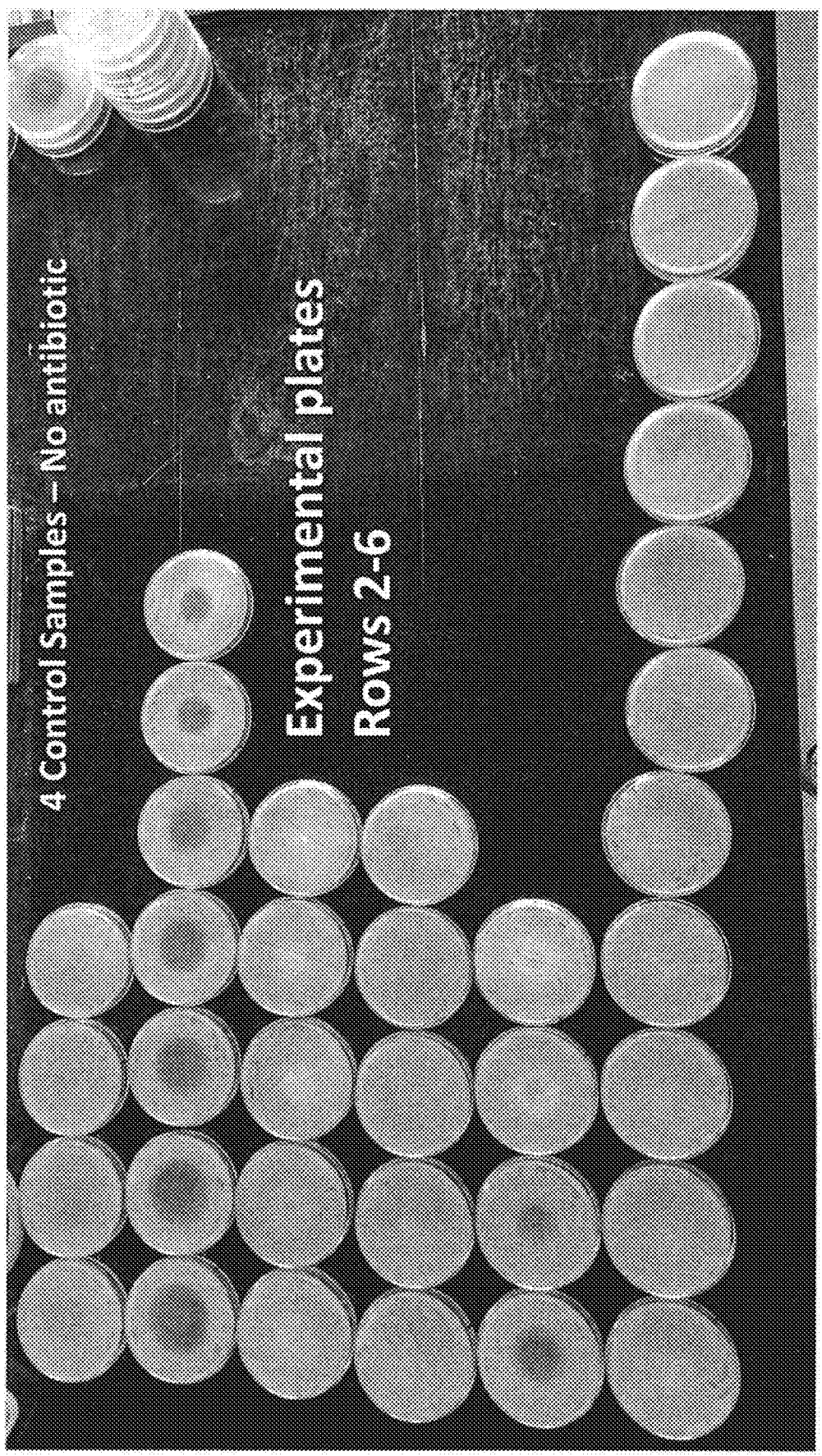
FIG. 7 is a photograph of plate cultures of *S. coelicolor*. The four plates in the top row are negative control plates receiving an aliquot of vehicle only, and that were not contacted with GBLs, showing that the vehicle affects neither growth nor antibiotic production. The plates in rows 2-6 were contacted with a racemic mixture of synthetic A-factor type GBLs indicated herein as X and XI as shown in FIG. 8.

Results with treated plate cultures and untreated plate controls not treated with GBLs are shown in FIGS. 3 and 7, in which pigmented antibiotic is produced only in response to treatment by the non-cognate synthetic non-naturally occurring GBL. FIGS. 3 and 7 are photographs of *S. coelicolor* in which positive antibiotic production was obtained as a result of increased amount of GBL applied to the respective plate.

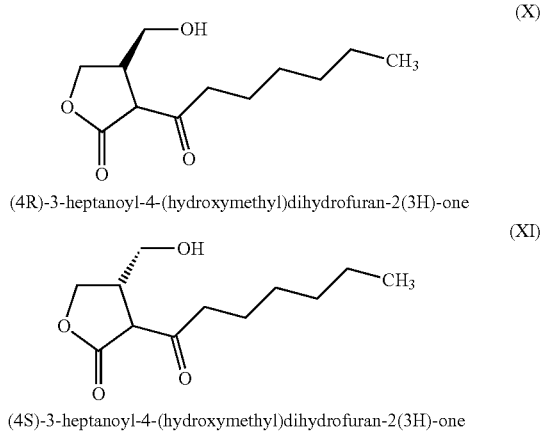

(4R)-3-heptanoyl-4-(hydroxymethyl)dihydrofuran-2(3H)-one (X)

(4S)-3-heptanoyl-4-(hydroxymethyl)dihydrofuran-2(3H)-one (XI)

Figure 12:
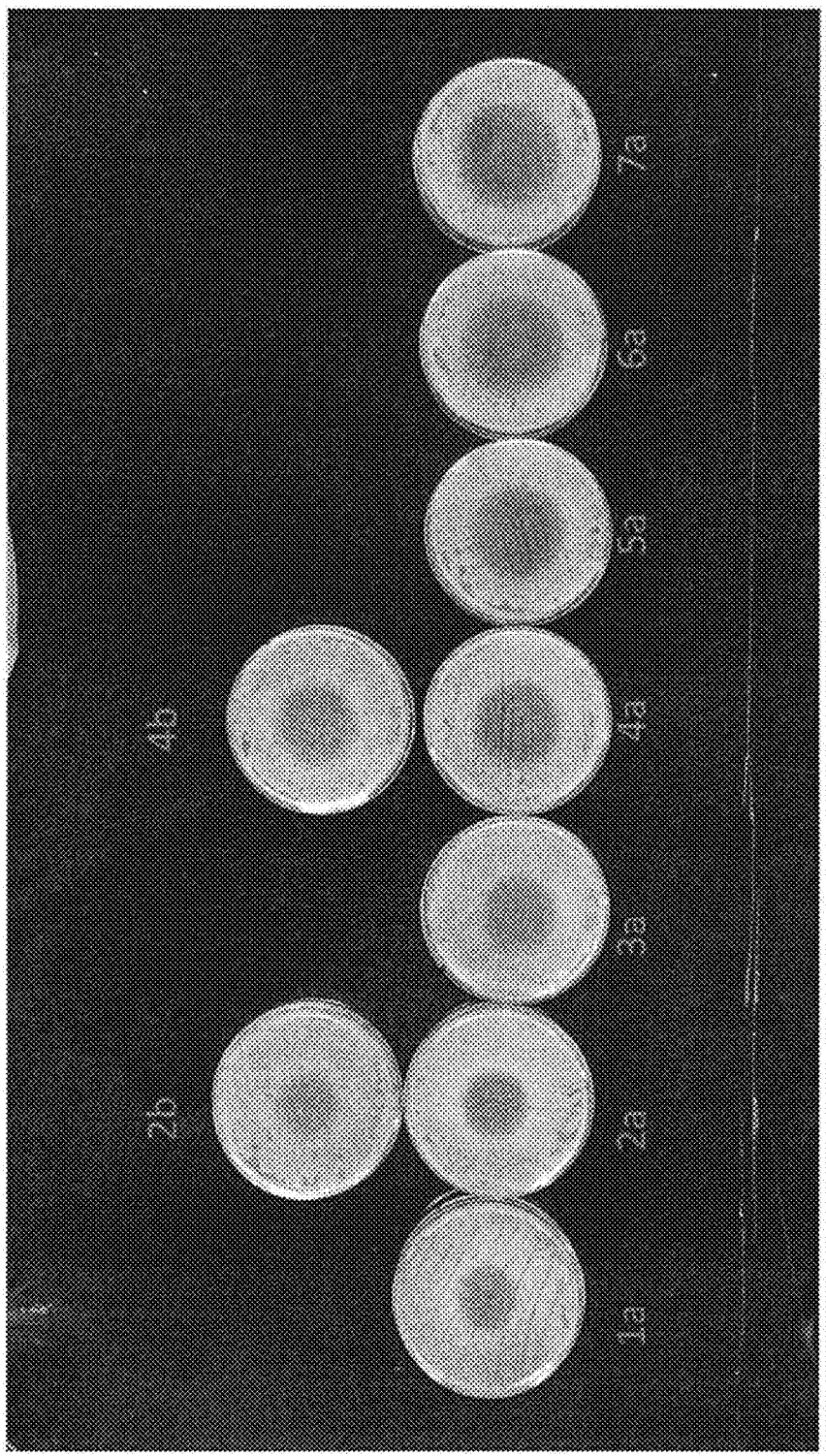
FIG. 12 is a photograph of the plates of FIG. 7 that yielded a positive effect, viz., actinorhodin production, arranged in order of increasing GBL dose from left to right.

FIG. 12 is a photograph of SMMS (supplemented minimal media solid) plates inoculated with a spore stock of *S. coelicolor* streaked to cover the surface of the medium in the plate. At the time of inoculation, 2 μL of a racemic solution containing each amount of a dilution of the racemic GBLs having formulas X and XI were deposited in the center of a plate. Plate 1a was spotted with 2 μL of a solution containing 16.5 μg of GBLs X and XI. Plates 2a and 2b were spotted with 2 μL of a solution containing 33 μg of GBLs X and XI. Plate 3a was spotted with a solution containing 49.5 μg of GBLs X and XI. Plates 4a and 4b were spotted with a solution containing 66 μg of GBLs X and XI. Plates 5a, 6a, 7a, were spotted with solutions containing 99 μg, 132 μg, and 165 μg of GBLs X and XI, respectively. Racemic mixture GBLs were present in equal molar amounts. The plates spotted with 16.5 μg, 33 μg, 49.5 μg, 66 μg, 99 μg, 132 μg, or 165 μg amounts of GBLs having formulas X and XI were observed to have increased production of pigmented antibiotics known to be produced by the strain *S. coelicolor* for which these GBLs are non-cognate. No pigment production was observed on the control plates shown in FIG. 7 not contacted with GBLs. Further, contacting the plates with GBLs was observed to result also in early induction of production of the pigmented antibiotics.

Example 7-Principal Component Analysis of *S. glaucescens* Cultured Under 96 Conditions of Media and GBL Supplementation

Figure 16:
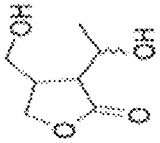
FIG. 16 is a drawing of chemical structures of GBLs used herein, contacted to cultures of microorganisms to determine effects on secondary metabolite production. There are eight enantiomeric stereoisomers of each of 3-(1-hydroxyethyl)-4-(hydroxymethyl)dihydrofuran-2(3H)-one and of 3-(1-hydroxyheptyl)-4-(hydroxymethyl)dihydrofuran-2(3H)-one, for example, see FIG. 10.

*S. glaucescens* cells were grown in 3 mL cultures under 96 different conditions of medium, GBL choice, and GBL concentration. Each GBL solution was added to a tube in each of the following concentrations: 0.2 μM, 0.8 μM, 4 μM, 20 μM, and 100 μM. Media were a minimal medium SMM or a yeast enriched complex medium R5 (also called R2YE). The GBL indicated in FIG. 17 as PR001 and PR002 are shown in FIG. 16, and have the chemical formulae, respectively: 3-(1-hydroxyethyl)-4-(hydroxymethyl)dihydrofuran-2(3H)-one; and, 3-(1-hydroxyheptyl)-4-(hydroxymethyl)dihydrofuran-2(3H)-one.

Fermentations were incubated in 24-well blocks (CR 424, Enzyscreen B.V., Netherlands) with lids (1221a), and were shaken at 200 rpm for 5 days at 28° C. in an Infors HT incubator (Infors AG, Switzerland). For analysis, a C18 SPE-IT tip (57234-U from Sigma-Aldrich) was added to each fermentation which were further shaken at 400 rpm for one hour. Tips were removed and rinsed in deionized water, and were analyzed directly or stored for analysis. Analysis was collected at ionsense, Inc. (Saugus, Mass.) vaporized with a DART source at 400 C and 1 mm/s, and mass spectral data collected in a Thermo LTQ. Analysis used Progenesis QI from Nonlinear Dynamics (Waters).

Figure 17:
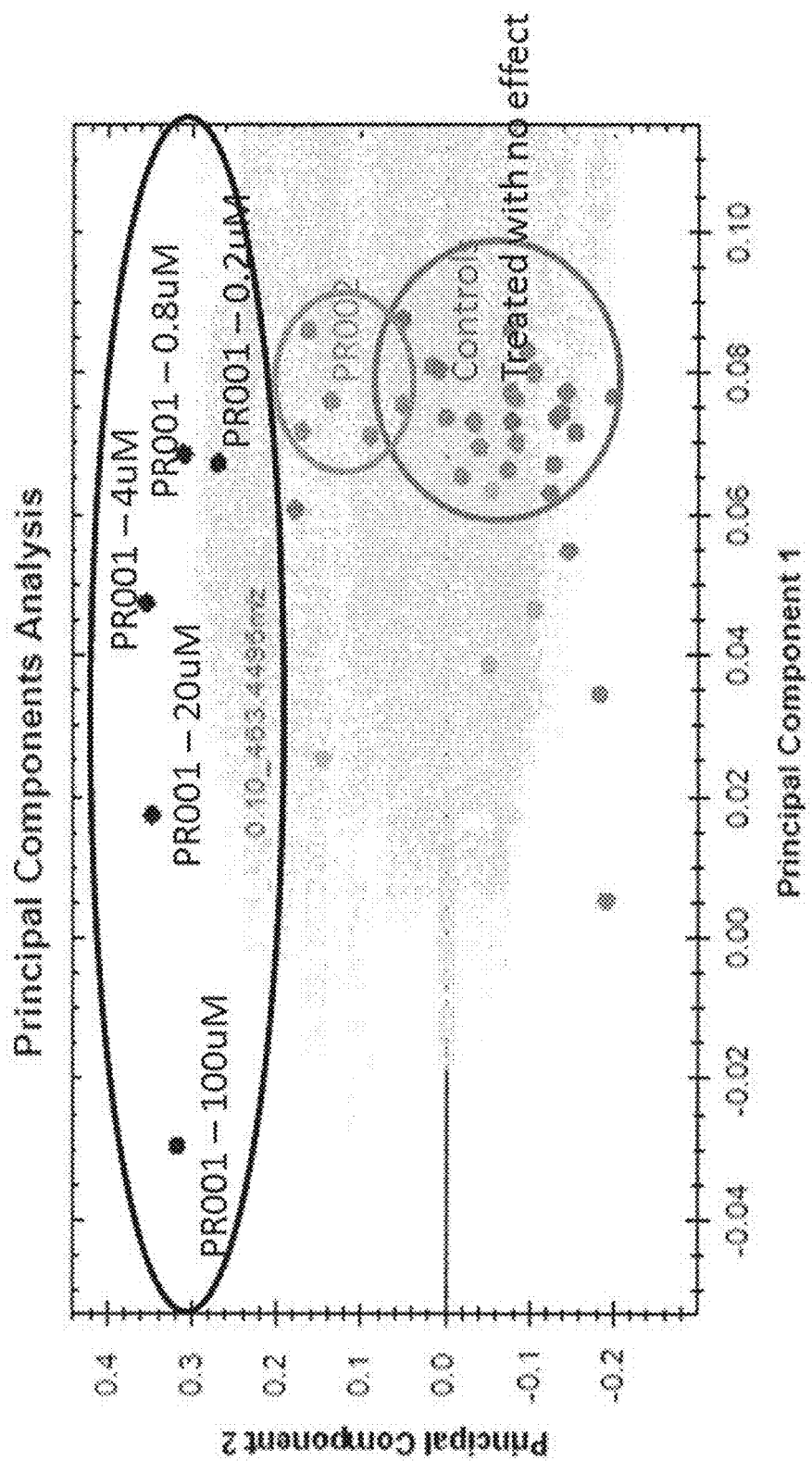
FIG. 17 is a display of principal component analysis using Progenesis QI software (Nonlinear Dynamics, Durham, N.C.). *S. glaucescens* was fermented in SMM medium and was treated with GBLs 3-(1-hydroxyethyl)-4-(hydroxymethyl)dihydrofuran-2(3H)-one (See, FIG. 16) and 3-(1-hydroxyheptyl)-4-(hydroxymethyl)dihydrofuran-2(3H)-one or a control untreated. LC-MS data of *S. glaucescens* fermentation cultures treated with GBLs 3-(1-hydroxyethyl)-4-(hydroxymethyl)dihydrofuran-2(3H)-one and 3-(1-hydroxyheptyl)-4-(hydroxymethyl)dihydrofuran-2(3H)-one and a control untreated *S. glaucescens* fermentation culture were analyzed. The GBL treated *S. glaucescens* show concentration dependent deviations of secondary metabolites produced compared to controls in compounds production. These results indicate induction of secondary metabolite production resulting from *S. glaucescens* treatment with 3-(1-hydroxyethyl)-4-(hydroxymethyl)dihydrofuran-2(3H)-one, in a dose-dependent manner, and with 3-(1-hydroxyheptyl)-4-(hydroxymethyl)dihydrofuran-2(3H)-one.

Principal component analysis data of secondary metabolites induced by the GBLs in comparison to control absent GBL are shown in FIG. 17. The two principal component concentrations of components 1 and 2 are displayed on ordinate and abscissa. The data revealed that greatest distinction from control secondary metabolites produced absent GBL was obtained by addition of 3-(1-hydroxyethyl)-4-(hydroxymethyl)dihydrofuran-2(3H)-one. Further, this induction was dose dependent, with maximal distinction obtained at 100 μM, and lesser distinction at each lower concentration. Accordingly, 100 μM GBL was used in large scale fermentions.

The initial large scale fermentation below was performed with *S. coelicolor* since this is a very well characterized species known to produce multiple antibiotics, to determine whether a synthetic non-cognate GBL, VB-D, and seven non-naturally occurring enantiomers, induce greater production of antibiotics and induce otherwise silent gene clusters to produce novel antibiotics.

Example 8—Identifying Novel Chemical Entities from Crude Extracts

Yields of both known and unknown bioactive compounds regulated by the presence of signaling hormones are improved by contacting producing cells with an appropriate GBL. Secondary metabolites were isolated from cultures of cells. Triplicate 300 mL cultures of *S. coelicolor* in SMM, was treated with the synthetic racemic mixture of VB-D and seven enantiomers of the non-cognate GBL shown in FIG. 10, at a total concentration of 100 μM, and an identical culture was grown without GBL. Cells were grown for five days at 29 C shaking at 220 rpm. Triplicates were pooled with GBL-treated and control cultures pooled separately.

A slurry of absorbent resins HP-20, XAD-16, XAD-7 and XAD-4 was added (2-4% weight/volume) and shaking was continued overnight. The resin and cell mass were removed by filtration and were washed three times with 200 mL deionized water. Resin and cell mass were extracted three times with 100-300 mL methanol to elute secondary metabolites from the resin. This extract was concentrated by rotary evaporation to remove extraction solvent.

The crude extract was dissolved in 1-3 mL of dimethylsulfoxide (DMSO) and was injected into a reveleris C18 reverse phase column on a Gilson High-Pressure Liquid Chromatography system. A flow rate of 15 ml/min was run for 40 minutes using mobile phases of methanol with 0.1% formic acid, and water with 0.1% formic acid. Forty-eight fractions were collected from a twenty minutes gradient of solvent from 15% methanol to 95% methanol, and were analyzed for antibacterial content on soft agar lawns of each of a Gram negative indicator strain, *Escherichia coli*, and a Gram positive indicator strain, *Bacillus subtilis*.

Further, 10 μL fraction volumes of each fraction were injected into a Waters Xevo G2-S Q-TOF LCMS system for further analytical separation and mass identification. Results are shown in Examples below.

Example 9—Bioassays of Fractions of Extracts

Fractions 1-48 of each of fractionated extracts of the GBL-treated and untreated control fermentations were assayed for antibacterial activity to obtain fractions showing activity as a result of the contact with the GBL. Results are shown in 17 and 18.

Figure 18:
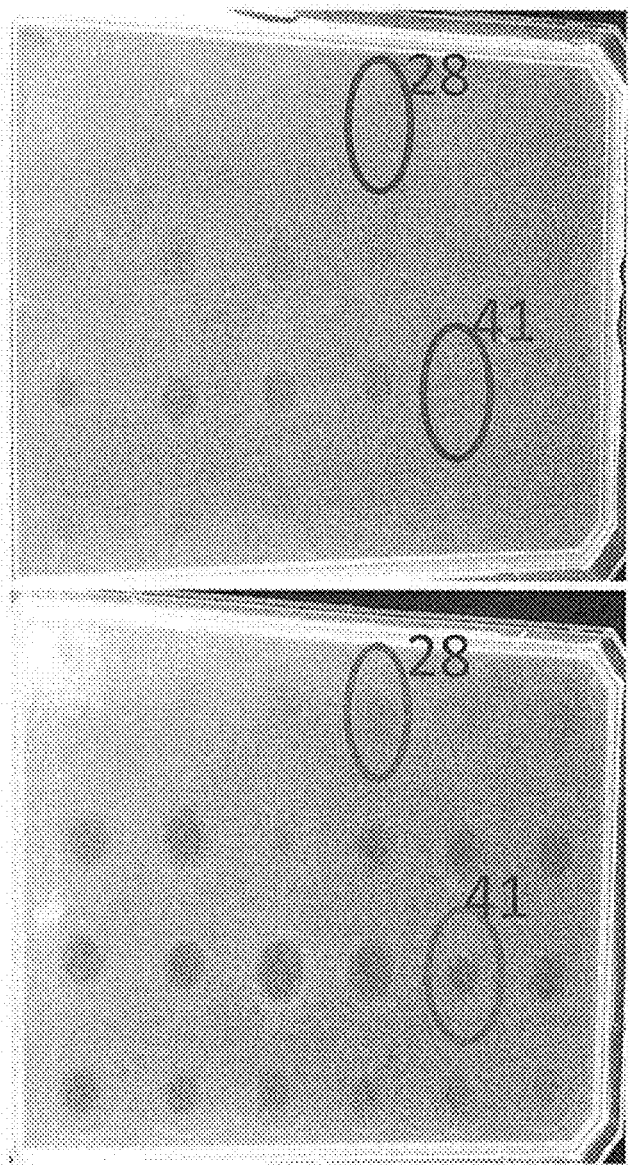
FIG. 18 are photographs of *Escherichia coli* confluent lawn in soft agar spotted with extracts of each of a *S. coelicolor* fermentation culture treated with 3-(1-hydroxyheptyl)-4-(hydroxymethyl)dihydrofuran-2(3H)-one (See, FIG. 10 and FIG. 16), and a control untreated *S. coelicolor* fermentation culture. Extracts were fractionated on an HPLC column. Fractions of the treated extract, particularly fractions 28 and 41, show strong bioactivity of 3-(1-hydroxyheptyl)-4-(hydroxymethyl)dihydrofuran-2(3H)-one treated in inducing the production of the anti-bacterial activity *S. coelicolor* killing *E. coli* bacteria as noted by circled zones. Strong antibacterial bioactivity resulted from induction of secondary metabolites by treatment of *S. coelicolor* with 3-(1-hydroxyheptyl)-4-(hydroxymethyl)dihydrofuran-2(3H)-one as seen compared to untreated *S. coelicolor*.

Control fractions data are shown in the top plate and GBL-treated fraction data shown in the bottom plate of FIG. 18, which are zones of killing of Gram negative *E. coli* cells. These plates start with fraction 25 assayed at the top left, and extend through fraction 48 at the bottom right of each plate. The results observed in these assays clearly show that fractions 28 and 41 of the GBL-treated extract contain at least one compound with antibacterial activity, and the corresponding fractions in the control extract does not.

Figure 19:
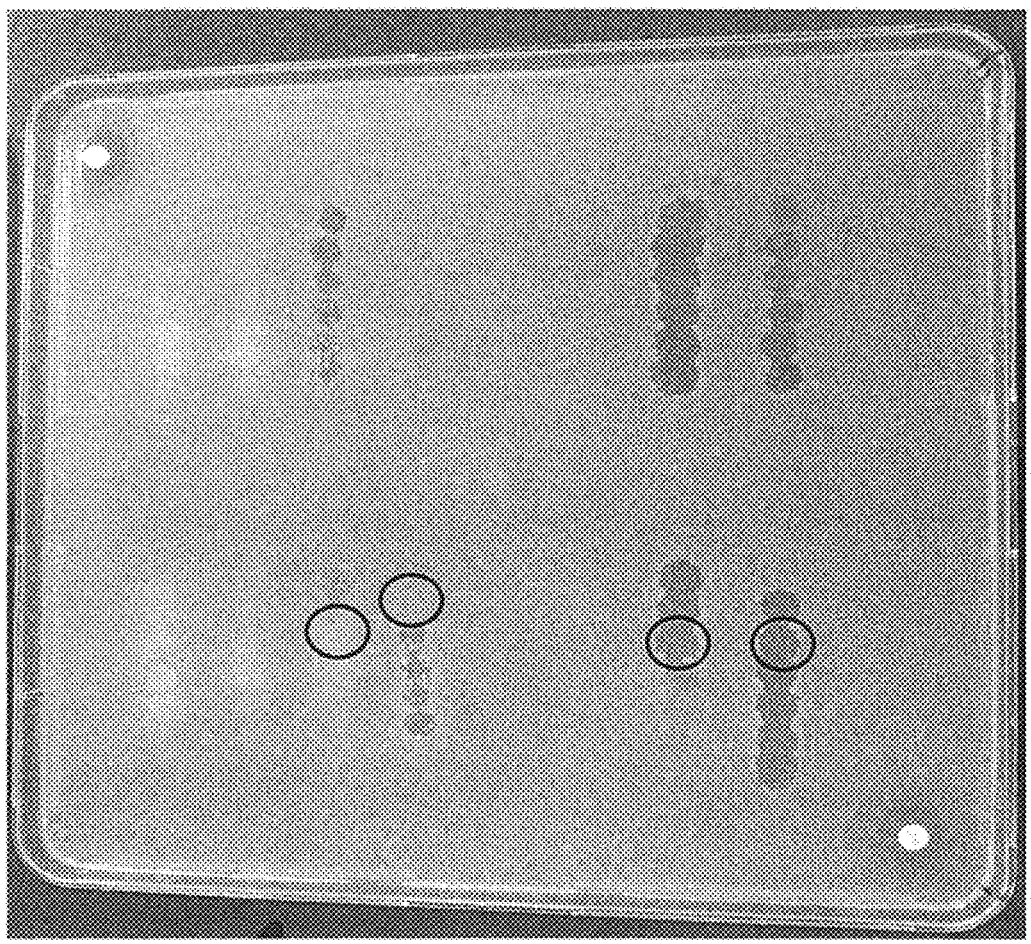
FIG. 19 is a photograph of a confluent lawn of *Bacillus subtilis* spotted with fractions of either a *S. coelicolor* fermentation culture treated with 3-(1-hydroxyheptyl)-4-(hydroxymethyl)dihydrofuran-2(3H)-one or a control untreated *S. coelicolor* fermentation culture. Zones of clearing, shown in circles, indicate antibacterial activity of at least one compound capable of killing *B. subtilis*. The results show appearance of antibacterial activity capable of killing *B. subtilis* by *S. coelicolor* culture treated with 3-(1-hydroxyheptyl)-4-(hydroxymethyl)dihydrofuran-2(3H)-one compared to untreated, particularly in fractions 28 and 41, shown in circles. These results indicate induction of secondary metabolites in the treated culture compared to untreated controls. A filter paper disk containing 10 μg of Streptomycin was placed in the upper right and lower left corners of the lawn.

Data in FIG. 19 with cells of Gram positive bacteria, *B. subilis*, are even more dramatic. Fractions 28 and 41 contain strong antibacterial activity in GBL-treated extracts, and the corresponding fractions from control extract failed to kill cells.

Accordingly, these fractions were analyzed by chemical techniques to further characterize the contents.

Example 10—Mass Spectroscopic Analysis of Antibacterial Fractions Induced by GBLS: Fraction 28

Figure 20:
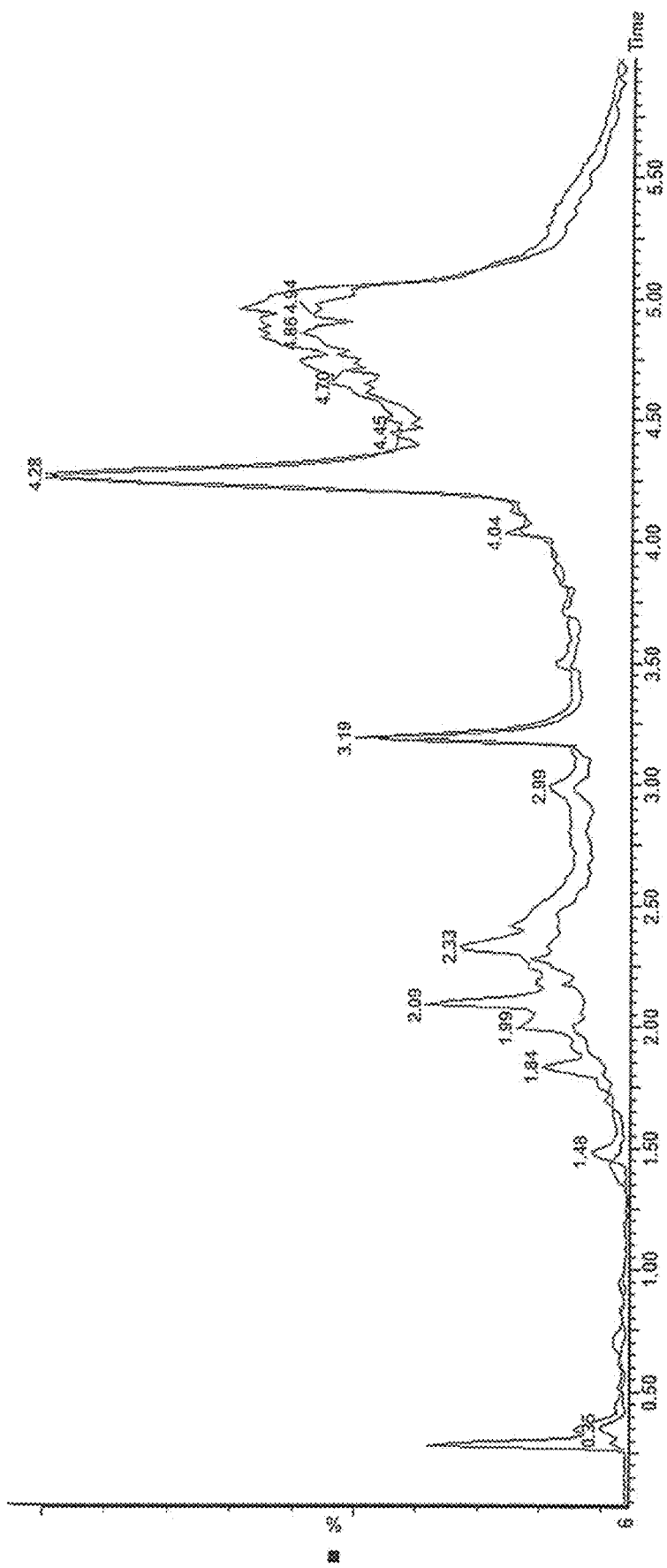
FIG. 20 is a mass chromatogram spectra of LC-MS data of fraction 28 (FIGS. 18 and 19) of an extract of each of a 300 mL *S. coelicolor* culture grown in SMM and treated with GBL 3-(1-hydroxyheptyl)-4-(hydroxymethyl) dihydrofuran-2(3H)-one and an untreated control, respectively. The LC-MS data was obtained using a Xevo G2-S Q-TOF mass spectrometer from Waters Corporation, Milford, Mass. The chromatogram trace with times of elution above the peaks indicates the treated fraction, and the trace below shows the control untreated fraction. Peaks showing compounds induced by addition of GBL 3-(1-hydroxyheptyl)-4-(hydroxymethyl)dihydrofuran-2(3H)-one were observed at retention times eluted at 1.48, 1.84, 1.99, 2.09 and 2.33. The peak at 1.84 was characterized as an unknown compound induced by *S. coelicolor* treatment with 3-(1-hydroxyheptyl)-4-(hydroxymethyl) dihydrofuran-2(3H)-one.
Figure 21:
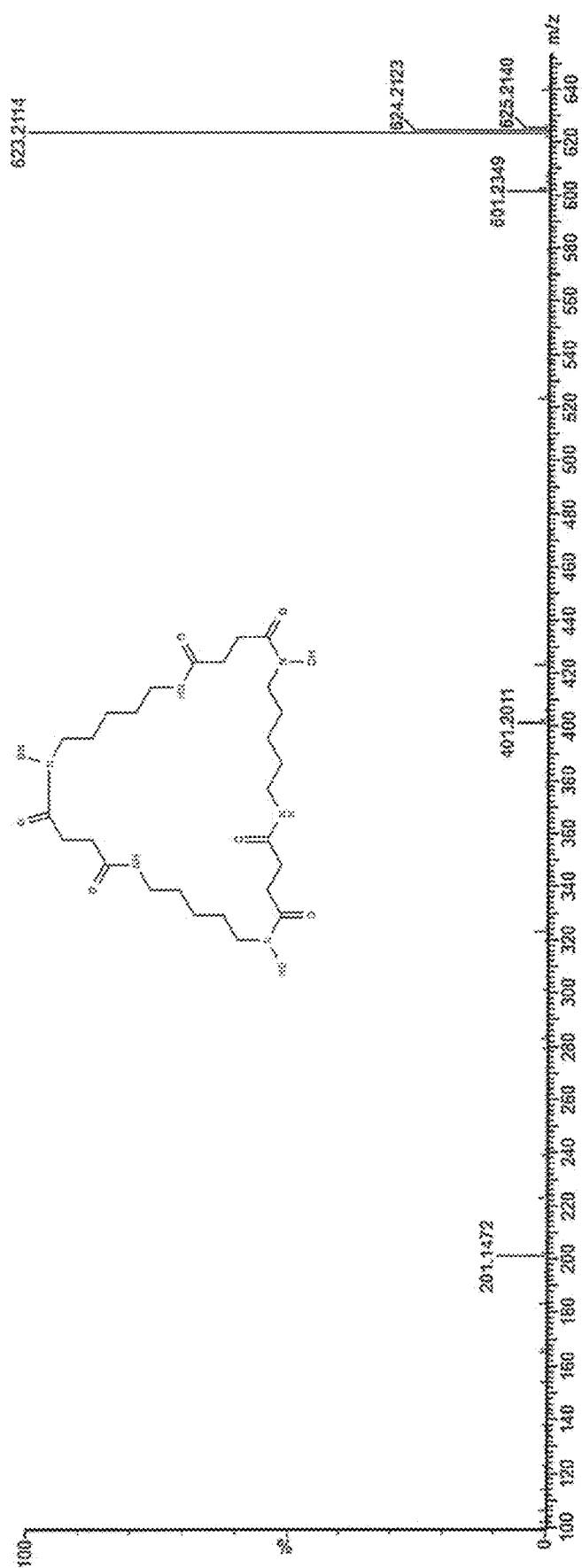
FIG. 21 is a mass chromatogram of the peak eluted at retention time 2.09 from fraction 28 in FIG. 20. The observed masses were determined to match those of iron-chelating compound Desferrioxamine E, see, Groenewold et al. "Collision-induced dissociation tandem mass spectrometry of desferrioxamine siderophore complexes from electrospray ionization of $UO_2^{2+}$, $Fe^{3+}$ and $Ca^{2+}$ solutions," *J Mass Spectrom* 39: 7, 752-761 (2004). The results show that Desferrioxamine E production was induced upon treating *S. coelicolor* culture with 3-(1-hydroxyheptyl)-4-(hydroxymethyl) dihydrofuran-2(3H)-one.
Figure 22:
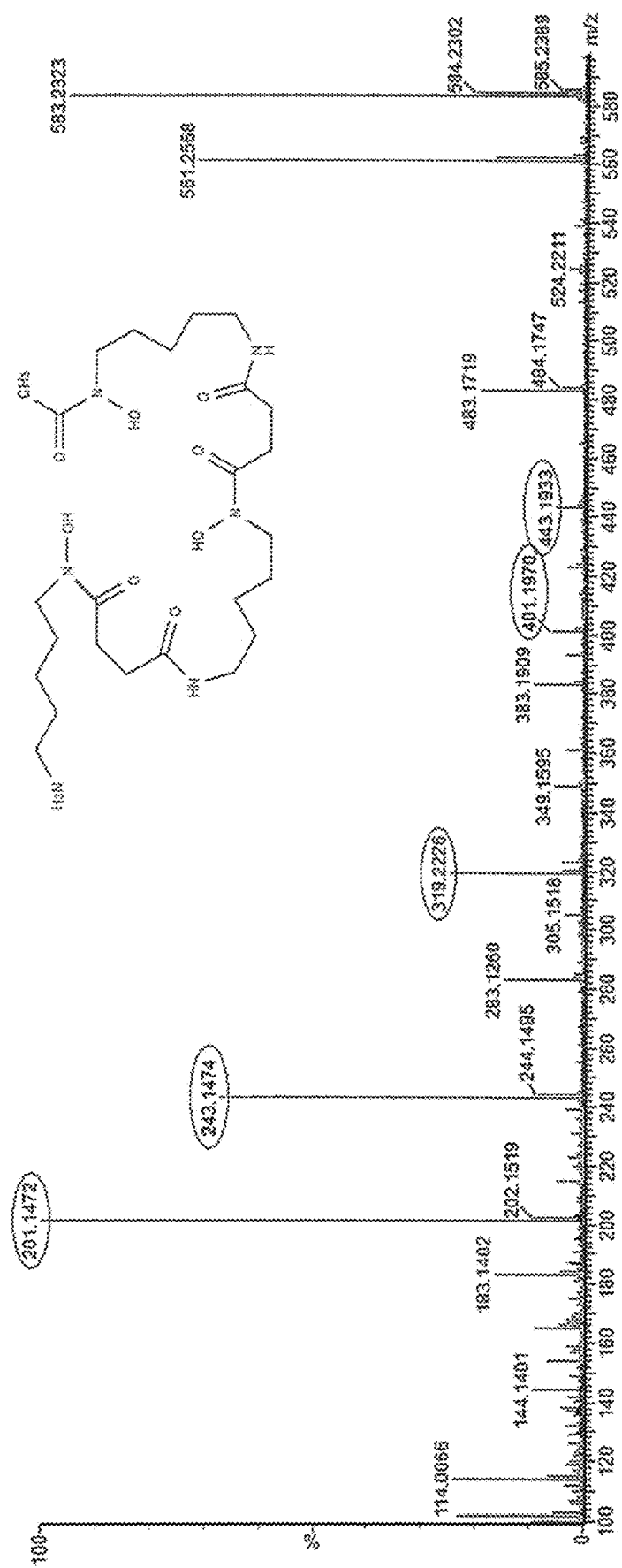
FIG. 22 is a mass chromatogram of the peak eluted at retention time 1.81 from fraction 28 in FIGS. 18, 19 and 20. The observed masses were determined to match those of iron-chelating compound Desferrioxamine B, see, Groenewold et al., Ibid. The results show that Desferrioxamine B production was induced by contact of *S. coelicolor* culture with 3-(1-hydroxyheptyl)-4-(hydroxymethyl) dihydrofuran-2(3H)-one.

Fraction 28 of each of the GBL and the control extracts were each analyzed by LC-MS-TOF. Data obtained with fraction 28 treated and controls superimposed are shown in FIG. 20. The trace for GBL-treated extract showed a greater total amount of material, and contained compounds with peaks eluting at time points 1.48, 1.84, 1.99, 2.09, and 2.33 which were not observed in the control extract.

The peak at retention time 2.09 was further analyzed by mass chromatogram, and it was observed that the parent masses and the fragmentation masses match that of the iron-chelating siderophore Desferrioxamine E the structure of which is shown in the figure above the data, as parent ion calculated mass 601.35 was observed. Daughter ions match that of published data.

The peak at retention time 1.81 was further analyzed by mass chromatogram, and it was observed that the parent masses and the fragmentation masses match that of the iron-chelating siderophore Desferrioxamine B the structure of which is shown in the figure above the data, as parent ion calculated mass is 560.34 and the observed mass is 561.26. Daughter ions match that of published data.

These data show that production of both Desferrioxamine B and Desferrioxamine E was substantially enhanced or even induced by the synthetic non-cognate GBL.

Figure 23:
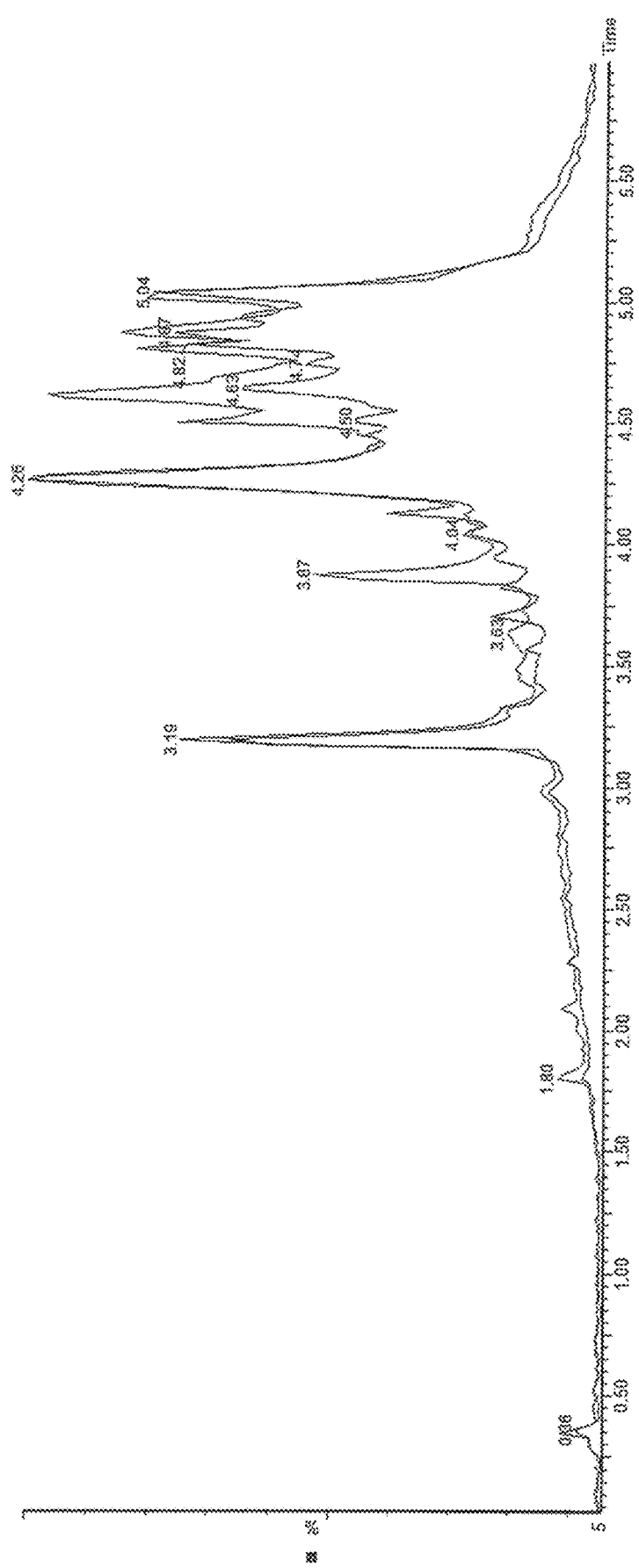
FIG. 23 is an mass chromatogram spectra of LC-MS data of fraction 41 as described in FIGS. 18, 19 and 20 of the cultures treated with 3-(1-hydroxyheptyl)-4-(hydroxymethyl) dihydrofuran-2(3H)-one and the untreated control. The chromatogram trace with time points above the peaks indicate the treated fraction, and the trace below shows the control untreated fraction. Peaks showing compounds induced by addition of 3-(1-hydroxyheptyl)-4-(hydroxymethyl) dihydrofuran-2(3H)-one were observed at retention times 3.87 and 3.63.
Figure 24:
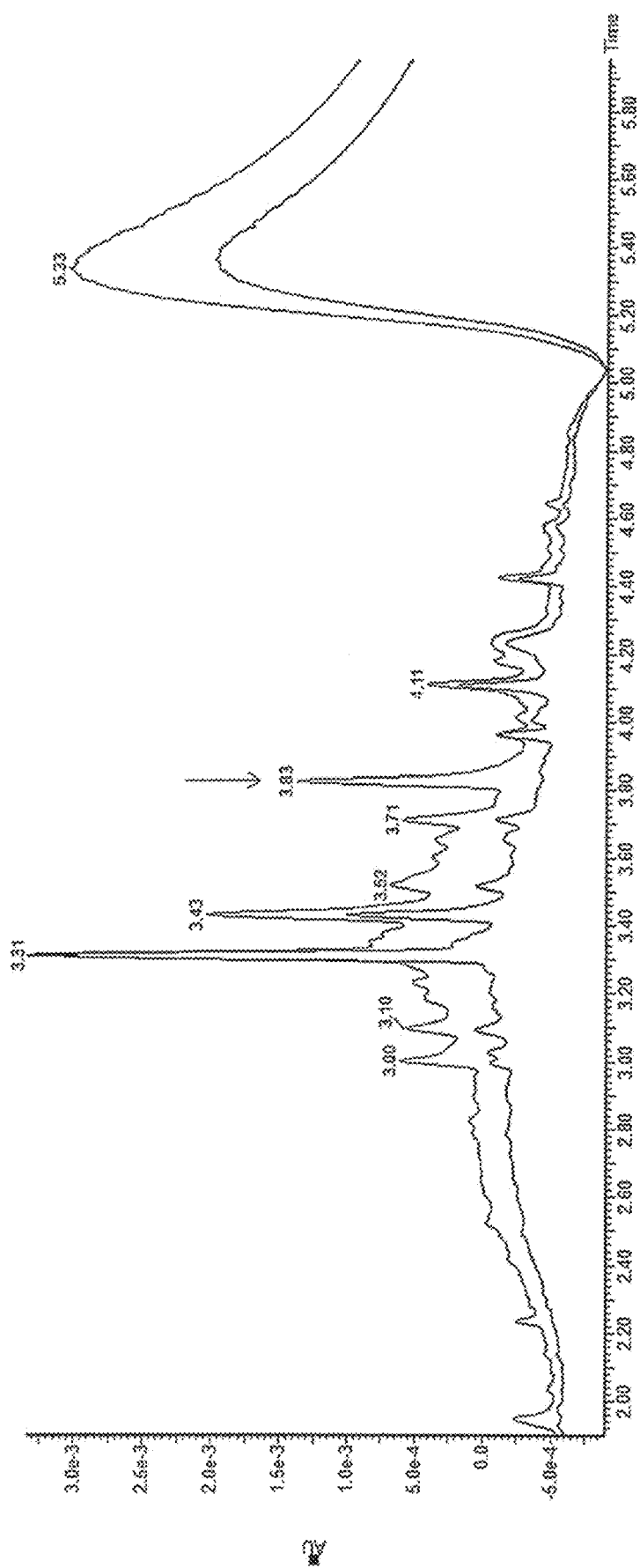
FIG. 24 is a UV chromatogram of diode array HPLC detector analysis of fraction 41 (FIGS. 18, 19, 20 and 23) of S. coelicolor cultures treated respectively with 3-(1-hydroxyheptyl)-4-(hydroxymethyl) dihydrofuran-2(3H)-one and untreated control. UV wavelength was set to 272 nanometers. The peak observed to elute at retention time 3.83 in the treated sample and not observed in the untreated control was determined to be undecylprodigiosin, a known antibiotic with anti-cancer and immunosuppressive properties. These results show that undecylprodigiosin production was induced by treatment of S. coelicolor with 3-(1-hydroxyheptyl)-4-(hydroxymethyl) dihydrofuran-2(3H)-one.
Figure 25:
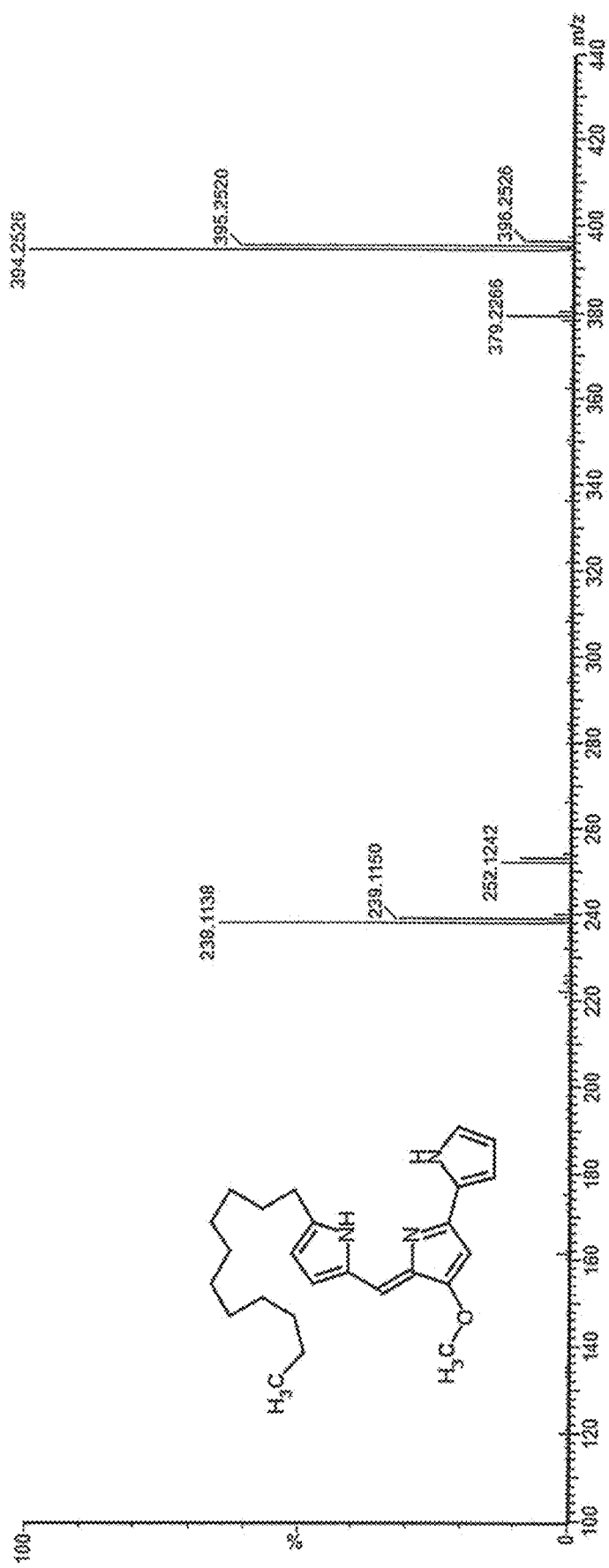
FIG. 25 is a mass chromatogram of peak at retention time 3.8 as observed in FIG. 23 and FIG. 24 from fraction 41. The observed masses were determined to match those of the antibiotic undecylprodigiosin, see, Chen et al., "Unusual odd-electron fragments from even-electron protonated prodiginine precursors using positive-ion electrospray mass spectrometry," *Journal of the American Society for Mass Spectrometry,* 19: 12, 1856-1866 (2008). The results show that undecylprodigiosin production was induced by treating S. coelicolor culture with 3-(1-hydroxyheptyl)-4-(hydroxymethyl) dihydrofuran-2(3H)-one.

Example 11—Mass Spectroscopic Analysis of Antibacterial Fractions Induced by GBLS: Fraction 41 and an Unknown Chemical Entity Fraction 41 of each of the GBL and the control extracts were each analyzed by LC-MS-TOF. Data obtained with fraction 41 treated and controls superimposed are shown in FIG. 23. The trace for GBL-treated extract showed a greater total amount of material, and contained compounds with peaks eluting at time points 1.80, 3.63, and 3.87 which were not observed in the control extract. Fraction 41 was subjected to UV chromatogram of diode array HPLC detector analysis. Again at prominent peak at 3.83 was observed. This material was determined to be undecylprodigiosin by mass chromatogram shown in FIG. 25, which has an observed mass of 393.27 and a calculated mass of 394.25. These data show that production of undecylprodigiosin was substantially enhanced or even induced by the synthetic non-cognate GBL.

Figure 26:
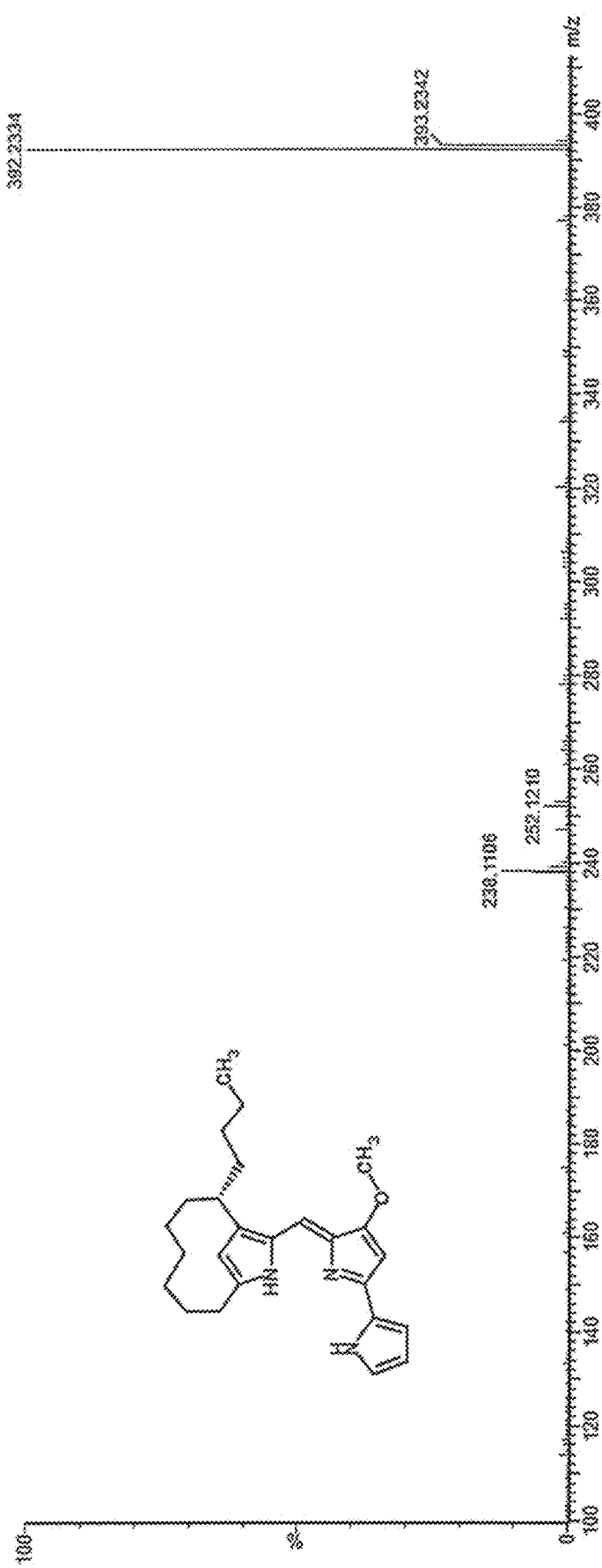
FIG. 26 is a mass chromatogram of the peak eluted at retention time 3.6 from fraction 41 in FIG. 23. The observed masses were determined to match those of the antibiotic streptorubin B, see Chen et al., Ibid. The results show that streptotubin B production was induced upon treating S. coelicolor culture with 3-(1-hydroxyheptyl)-4-(hydroxymethyl) dihydrofuran-2(3H)-one.

The peak in fraction 41 of 3.62 was determined to be Streptorubin B as shown in FIG. 26. This known antibiotic has a calculated mass of 391.26 and the mass observed here was 392.23. These data show that production of Streptorubin B was substantially enhanced or even induced by the synthetic non-cognate GBL.

The 1.84 peak of fraction 28 seen in FIG. 20 was analyzed, and is a potential novel chemical entity, as the data obtained do not correspond to literature reports.

Other microorganisms were subject to the small scale fermentations and principal component analyses to determine optimal GBL identification and concentrations, and to large scale fermentations as in the examples herein and the extracts obtained were subject to the chromatographic analyses performed above. Strains were chosen from Table I below, which is a list of suitable wild type or commercially interesting species, for small and large scale fermentations and extract analyses.

Embodiments of the method and composition having been fully described herein are further exemplified in the claims, which are not to be construed as further limiting. The contents of all references cited herein are hereby incorporated by reference in their entireties.

What is claimed is:

1. A method of improving a yield of a microbially-produced bioactive secondary metabolite product, the method comprising contacting cells of at least one strain of microorganism with a suitable amount of γ-butyrolactone (GBL) racemic mixture wherein the GBL is non-cognate to the strain, is synthetic, and is non-naturally occurring, and comprises two or more of the compositions selected from formulas I-VII

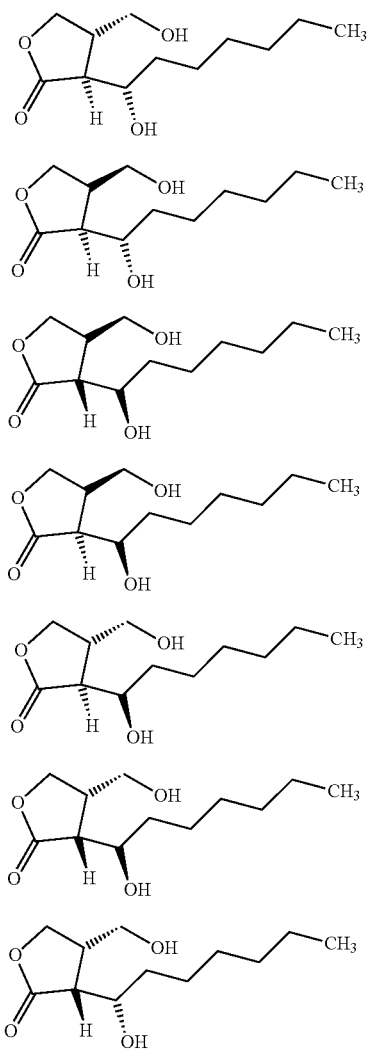

and culturing the cells of the strain with the GBL for production of the bioactive product; and, obtaining the product from the cells by separation of cells and medium or purification of the product from the cells and analyzing the amount of the product, wherein the yield of the product per unit of volume of culture or weight of cells is at least two-fold greater than that from control cells of the strain not contacted with the GBL compositions and otherwise identically cultured and analyzed, wherein the yield of the product from the cells cultured with the GBL is improved by at least two-fold compared to that from the control cells.

2. The method according to claim 1, wherein the strain of microorganism is bacterial.

3. The method according to claim 2, wherein the strain of bacteria is an actinomycete.

4. The method according to claim 1, wherein the strain of microorganism is fungal or algal.

5. The method according to claim 3, wherein a genus of the actinomycete selected from the group consisting of: *Actinopolyspora, Amycolatopsis, Micromonospora, Nocardia, Pseudonocardia, Saccharothrix, Saccharopolyspora, Salinospora, Streptomyces, Tetinomedara*, and *Verrucosispora*.

6. The method according to claim 1, wherein the yield of the product from the cells contacted with the GBL is at least about four-fold greater, ten-fold greater, or at least about twenty-fold greater than from the control cells.

7. The method according to claim 5, wherein the genus is *Streptomyces* and the species is selected from at least one of the group consisting of: *avermitilis, S. aureofaciens, S. capreolus, S. cattleya, S. clavuligerus, S. fradiae, S. garyphallus, S. kanamyceticus, S. levoris, S. lincolnensis, S. niveus, S. noursei, S. platensis, S. plicatus, S. pristinaespiralis, S. orientalis, S. ribosidifus, S. rimosus, S. roseosporus, S. scabiei, S. venezuelae*, and *S. vinaceus*; or is at least one *Pseudonocardia* selected from the group of: *P. acacia; P. ailaonensis; P. adelaidensis; P. alaniniphila; P. ammonioxydans; P. carboxydivorans; P. halophobia; P. kujensis; P. nitrificans; P. petroleophila; P. salamisensis; P. sulfoxidans; P. thermophila*; and *P. zigingensis*; or is at least one *Amycolatopsis* selected from the group of: *A. alba, A. azurea, S. balhimycena, A. coloradensis, A. fastidiosa, A. keratiniphila, A. lurida, A. mediterranei, A. orientalis, A. sulphurea, A. tolypomycina*, and *A. vancoresmycina*.

\* \* \* \* \*